(12) United States Patent
Rehwald et al.

(10) Patent No.: US 9,014,783 B2
(45) Date of Patent: Apr. 21, 2015

(54) SYSTEM FOR AUTOMATED PARAMETER SETTING IN CARDIAC MAGNETIC RESONANCE IMAGING

(75) Inventors: Wolfgang Rehwald, Chapel Hill, NC (US); Peter Weale, Chicago, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 862 days.

(21) Appl. No.: 12/721,591

(22) Filed: Mar. 11, 2010

(65) Prior Publication Data

US 2010/0268066 A1 Oct. 21, 2010

Related U.S. Application Data

(60) Provisional application No. 61/170,414, filed on Apr. 17, 2009.

(51) Int. Cl.
*A61B 5/055* (2006.01)
*G01R 33/56* (2006.01)
*G01R 33/567* (2006.01)
*A61B 5/00* (2006.01)

(52) U.S. Cl.
CPC ............ *A61B 5/055* (2013.01); *A61B 5/7285* (2013.01); *G01R 33/5602* (2013.01); *G01R 33/5676* (2013.01)

(58) Field of Classification Search
CPC .... A61B 5/055; A61B 5/7285; A61B 5/0044; A61B 5/0263; A61B 5/02007; A61B 5/0452
USPC .................................................. 600/407–429
See application file for complete search history.

(56) References Cited

U.S. PATENT DOCUMENTS

| 7,627,359 | B2 | 12/2009 | Yarnykh et al. |
| 2004/0133098 | A1 | 7/2004 | Yarnykh et al. |
| 2006/0184002 | A1 | 8/2006 | Yarnykh et al. |

*Primary Examiner* — Mark Remaly
(74) *Attorney, Agent, or Firm* — Peter R. Withstandley

(57) ABSTRACT

A system automatically calculates optimal protocol parameters for dark-blood (DB) preparation and inversion recovery. The system automatically determines pulse sequence timing parameters for MR imaging with blood related signal suppression. The system comprises an acquisition processor for acquiring data indicating a patient heart rate. A pulse timing processor automatically determines an acquisition time of an image data set readout, relative to a blood signal suppression related magnetization preparation pulse sequence, by calculating the acquisition time in response to inputs including, (a) the acquired patient heart rate, (b) data indicating a type of image contrast of the pulse sequence employed and (c) data indicating whether an anatomical signal suppression related magnetization preparation pulse sequence used has a slice selective, or non-slice selective, data acquisition readout.

21 Claims, 30 Drawing Sheets

10

Formula 1 (Non-Sel. RO With Slice-Sel or Non-Sel STIR)

1. Calculate time from center of non-sel. IR pulse of DB prep to center of STIR pulse:

dTimeDB2STIR_ms = dT1_BLOOD_MS * ln (2.0/(1.0 - 0.01*dM_STIRperc +
exp( ((double)lEchoTrainDuration_ms + dT1_FAT_MS - dDB_period_ms)/dT1_BLOOD_MS)) );

2. Calculate the current TR:
lCurrentTR_ms = dTimeDB2STIR_ms + dT1_FAT_MS+ lEchoTrainDuration_ms + dSTART2DBNSIR_MS

Figure 21

Formula 2 (Non-Sel. RO And Dark-Blood TSE)

1. Calculate dTimeDB2RO_ms:

dTimeDB2RO_ms = dT1_BLOOD_MS * ln(2.0/(1.0 + exp( (EchoTrainDuration_ms - dDB_period_ms)/dT1_BLOOD_MS)) )

2. Calculate lCurrentTR_ms :

lCurrentTR_ms = dTimeDB2RO_ms + lEchoTrainDuration_ms + dSTART2DBNSIR_MS

Figure 23

Formula 3 (Slice-Sel. RO With Non-Sel STIR)

1. Calculate magnetization required before STIR pulse so that blood is nulled at the beginning of the readout:

dM_BeforeSTIR_perc = dM0_PERC * ( exp(dTI_FAT_MS/dT1_BLOOD_MS) - 1.0 )

2. Calculate time from first NULL point of blood to STIR pulse
   dNull2STIR_ms = dT1_BLOOD_MS * ln( M0/(M0-dM_BeforeSTIR_perc) )

3. Calculate time from first NULL point of blood to beginning of readout:
   dNull2RO_ms = dNull2STIR_ms + dTI_FAT_MS 4. Calculate time from center of IR pulse of DB prep to the first NULL point of blood :
   dDB2Null_ms = dT1_BLOOD_MS * log( 2.0/(1.0 + dE) )

where dE = exp ( (-1*dDB_period_ms + dNull2RO_ms)/dT1_BLOOD_MS )

5. Calculate current TR:
   lCurrentTR_ms = dSTART2DBNSIR_MS + dDB2Null_ms + dNull2RO_ms + lEchoTrainDuration_ms;

Figure 25

Formula 4 (Slice-Sel. RO With Slice-Sel STIR)

1. Determine dM_BeforeDB_perc (magnetization in percent of M0 prior to inversion by non-sel IR of DB-prep):
M(t) = M0 + (-dM_BeforeDB_perc - M0) exp(- dDB_period_ms/dT1_BLOOD_MS) = dM_BeforeDB_perc

=> dM_BeforeDB_perc = M0 *(1. - exp(-1.*dDB_period_ms/dT1_BLOOD_MS))/(1. + exp(-1.*dDB_period_ms/dT1_BLOOD_MS))

2. Determine magnetization required before STIR pulse so that blood is nulled at the beginning of the readout:

dM_BeforeSTIR_perc = dM0_PERC *( exp(dT1_FAT_MS/dT1_BLOOD_MS) - 1.0 )

3. Determine the time between the center of the non-sel IR of the DB prep module and the center of the STIR pulse:
dTimeDB2STIR_ms = dT1_BLOOD_MS * ln ( (M0 + dM_BeforeDB_perc) / (M0 - dM_BeforeSTIR_perc) )

4. Calculate time between the center of the non-sel IR of the DB prep module and the start of the readout:
dTimeDB2RO_ms = dTimeDB2STIR_ms + dT1_FAT_MS;

5. Calculate current TR:
lCurrentTR_ms = dSTART2DBNSIR_MS + dTimeDB2RO_ms + lEchoTrainDuration_ms;

Figure 27

Formula 5 (Slice-Sel. RO And Dark-Blood TSE)

1. Determine dM_BeforeDB_perc (magnetization in percent of M0 prior to inversion by non-sel IR of DB-prep):

$M(t) = M0 + (-dM\_BeforeDB\_perc - M0) \exp(- dDB\_period\_ms/dT1\_BLOOD\_MS) = dM\_BeforeDB\_perc$ $dM\_BeforeDB\_perc = M0 *(1. - \exp(-1.*dDB\_period\_ms/dT1\_BLOOD\_MS))/(1. + \exp(-1.*dDB\_period\_ms/dT1\_BLOOD\_MS))$ 2. Determine dTimeDB2RO_ms (time from center of non-sel IR of DB-prep to beginning of RO):
dTimeDB2RO_ms = dT1_BLOOD_MS * ln ( (M0 + dM_BeforeDB_perc)/M0)

3. Calculate current TR:
lCurrentTR_ms = dSTART2DBNSIR_MS + dTimeDB2RO_ms + lEchoTrainDuration_ms

Figure 29 ically moved out of the slice and been replaced by inverted
SYSTEM FOR AUTOMATED PARAMETER SETTING IN CARDIAC MAGNETIC RESONANCE IMAGING This is a non-provisional application of provisional application Ser. No. 61/170,414 filed 17 Apr. 2009, by W. Rehwald et al.

FIELD OF THE INVENTION

This invention concerns a system for automatically determining pulse sequence timing parameters for MR imaging with blood related signal suppression involving calculating an image acquisition time in response to multiple inputs.

BACKGROUND OF THE INVENTION

Dark blood preparation (DB-prep) also known as "Double Inversion Recovery" (double IR) magnetization preparation, is commonly used in cardiac and vascular MRI (magnetic resonance imaging) for reducing or eliminating MRI signal data associated with blood. The known method relies upon effective inversion of the intra-cardiac or intra-vascular blood signal by the application of a pair of inversion pulses, initially a non-selective inversion pulse is followed immediately by a slice-selective inversion pulse where the slice to be imaged is re-inverted. The effect of this pair of inversion pulses is to invert the blood outside the slice to be imaged and to leave the imaged slice effectively untouched as if it had not experienced any change from its original condition. The inverted blood recovers its longitudinal magnetization during the inversion time and the slice is then imaged using one of a variety of MRI pulse sequences, typically a variant of the Turbo Spin-Echo (TSE) type. During this inversion time the blood which has experienced both inversion pulses has typically moved out of the slice and been replaced by inverted blood, as illustrated in FIG. 1. The inversion slice is usually thicker than the imaged slice (e.g. twice as thick). This is to ensure that the imaged slice is untouched even in the setting of an imperfect registration between DB-preparation slice and imaged slice.

A known system acquires imaging data (also known as data readout, RO) during the period where the longitudinal magnetization of the inverted blood is passing through a zero point and cannot contribute any signal to the image. This is called blood nulling. A representative timing of the electro cardiogram (ECG), recovery curve of the longitudinal magnetization $M_Z$ of the blood, DB-preparation module, and time of data readout relative to the recovery curve and ECG are illustrated in FIG. 2. However the inversion time required for complete blood nulling is dependent on the T1-relaxation time of the blood, which is predictable and largely constant, as well as the time between the repetitions of the DB-preparation module (specifically the non-selective inversion within the DB-preparation) which, in turn, is dependent upon the heart rate of the patient.

In a known method for acquiring images in cardiac MR, the DB-preparation module is played repeatedly in a periodic manner as data is collected in small segments over several heart beats where the imaging sequence is synchronized with an ECG, so that the heart is spatially positioned substantially identically for the collection of each segment of data. For optimal timing, the shorter the time between two consecutive DB-preparation modules, the shorter the effective inversion time to null blood. The time between the DB-preparation modules depends on a trigger pulse which determines whether single R-waves (trigger pulses 1), alternating R-waves (trigger pulses 2), or every nth R-wave (trigger pulses n) are used for triggering. The trigger pulse is usually adjusted by a scanner operator as a function of patient heart rate. While the theoretical timing for inversion and readout are predictable using known equations for simulation of the MR signal, the practicality of manually changing the sequence timing dependent on heart rate means that for most situations operators live with sub-optimal blood nulling, or spend a lot of time trying to optimize the blood nulling for the patient heart rate at the expense of scanning efficiency.

In dark-blood preparation, the correct repetition time TR (unlike in MR physics, TR in this document is defined as the time from the start of the DB-preparation module until the end of the readout, as shown in FIG. 2) is determined as the normal TR values achieved with patients within the normal range of heart rates are sufficient to allow inversion times encompassed within one RR interval to result in reasonably good blood nulling (the RR interval is the time from one R-wave to the next, i.e., the heart beat duration). This is not the case, however, in patients with very fast heart rates and especially if a third inversion pulse, the STIR pulse, is used to prepare the magnetization of an imaging slice. The third IR pulse might be played, for example, to impart a T1 plus T2 contrast and is commonly called Short tau Inversion Recovery (STIR). The inversion time of the STIR pulse is chosen to null fat and to impart a T1 contrast to the image. This can be achieved by use of a selective or non-selective inversion preparation. In known systems selective preparation is used for the STIR pulse to avoid compromised dark blood preparation and the timing with a slice-selective preparation is the same as if no STIR pulse were used.

In known dark-blood preparation (DB prep) shown in FIG. 2, blood is black or dark because the magnetization of the blood that recovers exponentially is imaged at the point in time when the recovery curve is at about zero ("nulled"). That is where the data readout starts. Zero magnetization means zero MR signal which is depicted as black in an image. Very positive or very negative magnetization both show up bright in an MR image. The magnetization assumes values from $-100\%$ of M0 to $+100\%$ of M0. M0 is the magnetization of the patient (blood and tissue) due to a strong magnetic field created by an MRI scanner. Dark blood preparation comprises inverting the magnetization outside a prepared slice so that it can recover according to the exponential recovery curve of FIG. 2. The tissue and blood inside the slice is re-inverted substantially immediately after the non-selective inversion so that it is left magnetically unaltered. It is at $+100\%$ of M0, whereas blood is at about $-100\%$ and recovers back to $+100\%$ over time. At the time of readout the blood that was in the slice during the DB preparation has left the slice due to cardiac contraction expelling blood, and the blood from outside the slice has moved inside. Now in this slice blood and tissue are magnetized differently. By timing readout, the blood magnetization is zero, hence blood appears dark and contrast between blood and tissue is emphasized. A system according to invention principles addresses the problems involved in providing pulse sequence timing in Dark blood MR imaging applications.

SUMMARY OF THE INVENTION

A system automatically calculates optimal protocol parameters for dark-blood (DB) preparation and inversion recovery including timing parameters, temporal resolution (also called shot time), dark blood thickness, and trigger pulse parameters for pulse sequences as a function of patient heart rate simplifying operation of the pulse sequences by an MRI scanner operator and improving image quality for different heart rates. A system automatically determines pulse sequence timing parameters for MR imaging with blood related signal suppression. The system comprises an acquisition processor for acquiring data indicating a patient heart rate. A pulse timing processor automatically determines an acquisition time of an image data set readout, relative to a blood signal suppression related magnetization preparation pulse sequence, by calculating the acquisition time in response to inputs including, (a) the acquired patient heart rate, (b) data indicating a type of desired image contrast of the pulse sequence employed and (c) data indicating whether an anatomical signal suppression related magnetization preparation pulse sequence used has a slice selective, or non-slice selective, data acquisition readout.

BRIEF DESCRIPTION OF THE DRAWING

FIGS. 20-29 show adaptively selectable formulas 1-5 and associated pulse sequence timing characteristics for use in calculating TR for dark blood imaging in response to multiple different inputs, according to invention principles.

DETAILED DESCRIPTION OF THE INVENTION

Figure 1:
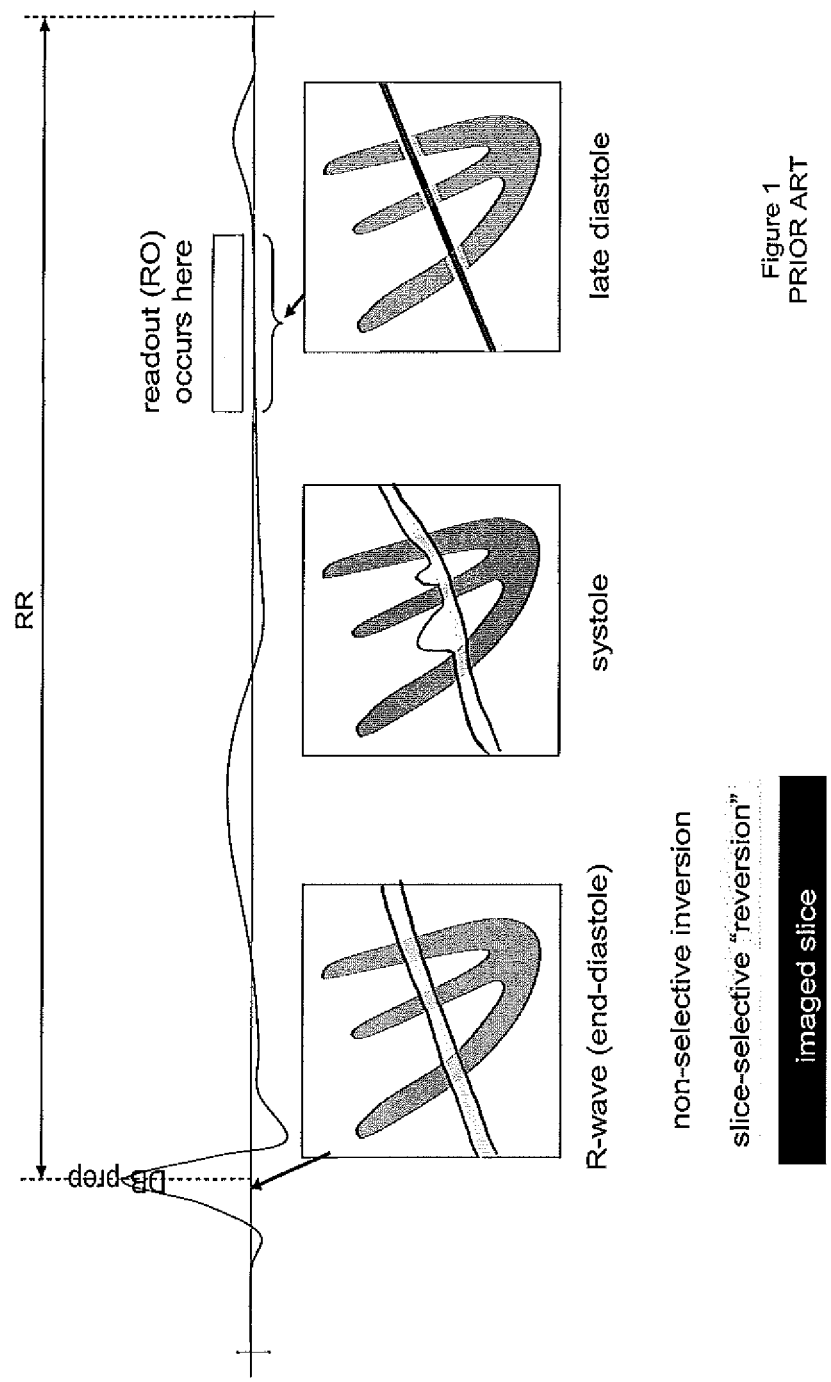
FIG. 1 illustrates known dark blood preparation using a double inversion pulse sequence.
Figure 2:
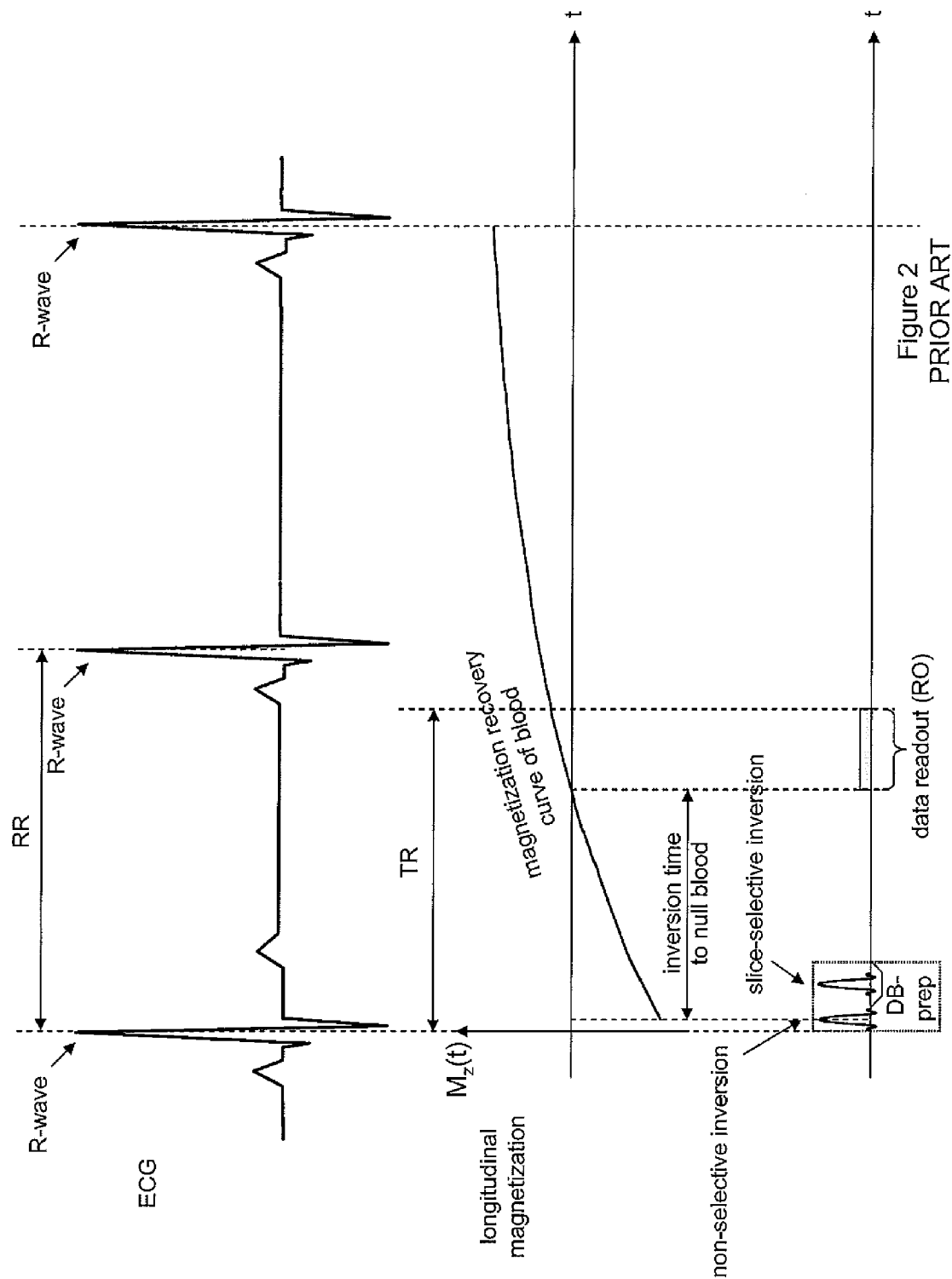
FIG. 2 shows known relative timing of an ECG signal, magnetization recovery curve, DB preparation and associated readout.

A cardiac Magnetic Resonance Imaging (MRI) system employs dark-blood (DB) and dark-blood inversion recovery (e.g., STIR (short tau inversion recovery)) pulse sequences. The system automatically calculates optimal protocol parameters including timing parameters, temporal resolution (also called shot time), dark blood thickness, and trigger pulse parameters for the pulse sequences as a function of patient heart rate simplifying operation of the pulse sequences by an MRI scanner operator and improving image quality for different heart rates. The inventors have advantageously recognized that significantly improved clinical results are achieved if the STIR is non-selective rather than a slice-selective STIR pulse. However, if a non-selective inversion is applied to a partially recovered blood pool magnetization, the timing for optimal blood signal reduction is more complex and not easily understood by a scanner operator. Finding the optimal timing as function of the heart rate is counterintuitive and requires understanding of the non-linearity of the problem.

The system provides an automated calculation of pulse sequence parameter timing and addresses the different timing requirements of non-selective STIR, for example, by intelligent selection of optimal scan parameters based not only on well known Bloch equations, but also by incorporating knowledge of optimal physiological timing of data acquisition which is normally required to occur during a period of a cardiac cycle when motion is minimal, typically at end of diastole. The automated calculation may be advantageously performed for DB-preparation with, and without, non-selective STIR.

Known system parameter timing may assume an optimal condition where desirable TI and TR are constrained to be within one heart beat. However, for a wide range of heart rates the TR and TI achievable when using two RR intervals for the repetition time, fit within one RR, because MR physics and physiology work in tandem to yield acceptable blood nulling. However, at very high heart rates, as seen in children or with the inclusion of a third non-selective inversion, which has significant advantages over a selective preparation in terms of signal homogeneity, the correct TI and TR may no longer be achievable within one RR interval.

In order to achieve required timing while maintaining advantageous positioning of data acquisition in a diastolic minimal-motion period, a more complex adjustment of scan timing parameters is required. This includes determining a time delay between an R-wave and dark blood preparation, and between the DB-preparation and the data acquisition. The system performs single, double, and triple-RR interval imaging (DB-preparation and readout occur in the same, in two, or in three heart beats, respectively), for example. The system automated calculation of timing and other parameters provides required adjustments. Additionally the quality of an acquired image may depend on the duration within which data is acquired in a cardiac cycle. In fast heart rates it is advantageous to reduce the time during which data is acquired within a heart beat at the expense of needing more heart beats to acquire the data. The system also advantageously determines an intelligent optimization of this period, the "shot duration".

DB-preparation is typically combined with slice-selective STIR. However this has clinical limitations due to slice registration error between a read out slice and the STIR slice. In order to overcome this error, the system advantageously combines DB-preparation with non-selective STIR. This is counter-intuitive, as the blood outside the slice now does not only see the non-selective inversion of the DB-prep, but also the non-selective STIR inversion pulse. This causes a confusing change in timing and the system advantageously uses an automatic timing processor to determine an automated setting of the timing.

The system advantageously provides dark-blood imaging with non-selective STIR for cardiovascular application, for example. The system timing processor provides automatic timing, which is used to set the timing correctly for dark-blood imaging with non-selective STIR (i.e., so that blood is black in the image). The automatic timing, is advantageously used not only for dark-blood imaging with non-selective STIR, but also for dark-blood imaging without STIR and for dark-blood imaging with slice-selective STIR. For each of these cases the relaxation curves of blood are different, and the system adaptively determines a timing calculation formula for determining repetition time TR. Further data read out also affects the magnetization curves of blood. Using non-selective refocusing as part of the readout resets the blood signal to zero after the readout. The combinations of no STIR, selective STIR and non-selective STIR together with the different types of readout (selective versus non-selective refocusing) provide different timing cases addressed for exemplary purposes herein.

Figure 3:
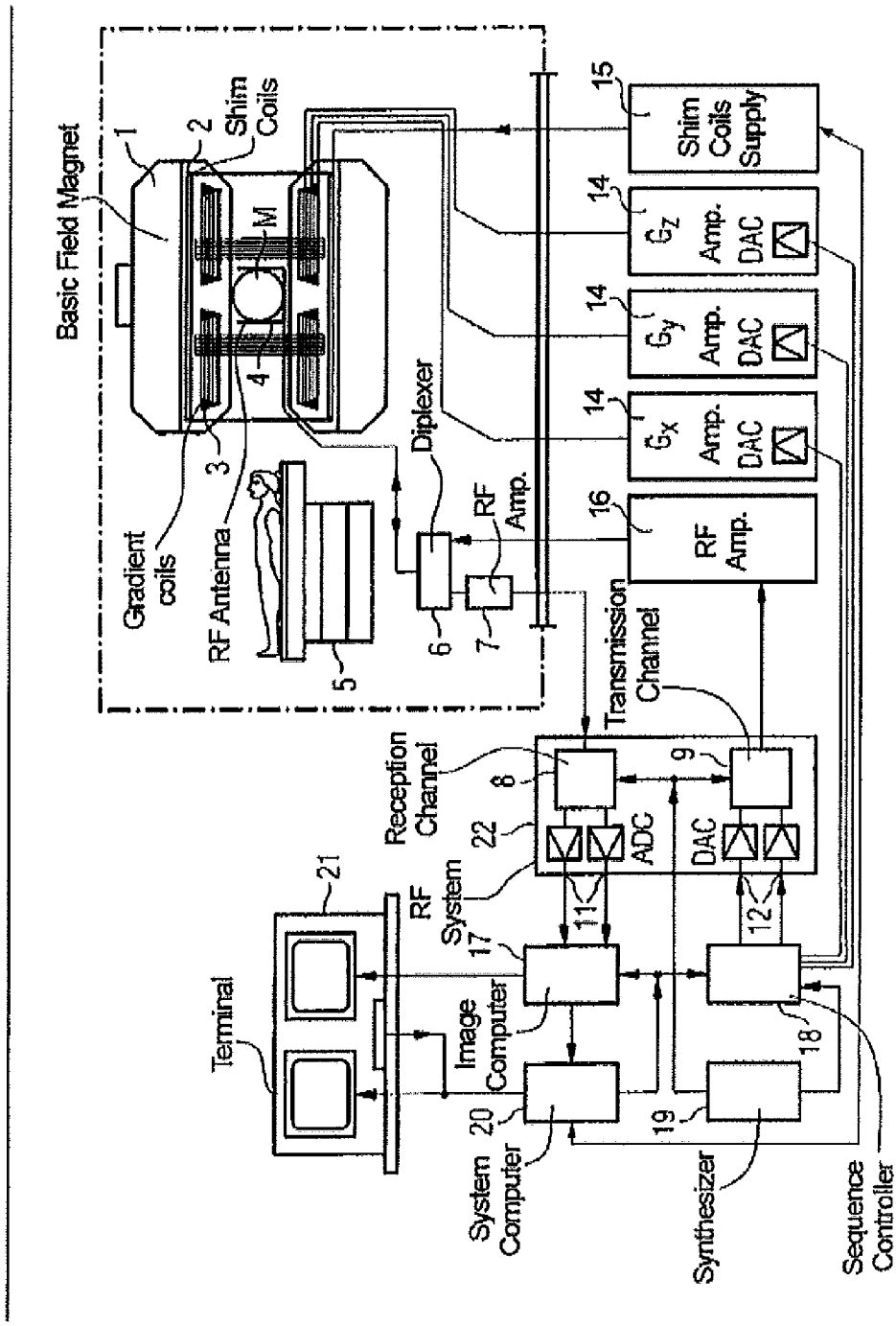
FIG. 3 shows a system for automatically determining pulse sequence timing parameters for MR imaging with blood related signal suppression, according to invention principles.

FIG. 3 is a schematic block diagram of a system 10 including a magnetic resonance tomography device with which MR images can be acquired according to principles of the present invention. A basic field magnet 1 generates a strong magnetic field, which is constant in time, for the polarization or alignment of the nuclear spins in the examination region of an object, such as, for example, a part of a human body to be examined. The high homogeneity of the basic magnetic field required for the magnetic resonance measurement is provided in a spherical measurement volume M, for example, into which the parts of the human body to be examined are brought. In order to satisfy the homogeneity requirements and especially for the elimination of time-invariant influences, shim-plates made of ferromagnetic material are mounted at suitable positions. Time-variable influences are eliminated by shim coils 2, which are controlled by a shim-current supply 15.

In the basic magnetic field 1, a cylinder-shaped gradient coil system 3 is used, which consists of three windings, for example. Each winding is supplied with current by an amplifier 14 in order to generate a linear gradient field in the respective directions of the Cartesian coordinate system. The first winding of the gradient field system 3 generates a gradient $G_x$ in the x-direction, the second winding generates a gradient $G_y$ in the y-direction, and the third winding generates a gradient $G_z$ in the z-direction. Each amplifier 14 contains a digital-analog converter, which is controlled by a sequence controller 18 for the generation of gradient pulses at proper times.

Within the gradient field system 3, radio-frequency (RF) coils 4 are located which converts the radio-frequency pulses emitted by a radio-frequency power amplifier 16 via multiplexer 6 into a magnetic alternating field in order to excite the nuclei and align the nuclear spins of the object to be examined or the region of the object to be examined. In one embodiment, RE coils 4 comprise a subset or substantially all of, multiple RF coils arranged in sections along the length of volume M corresponding to the length of a patient. Further, an individual section RE coil of coils 4 comprises multiple RE coils providing RF image data that is used in parallel to generate a single MR image. RF pulse signals are applied to RF coils 4, which in response produces magnetic field pulses which rotate the spins of the protons in the imaged body by ninety degrees or by one hundred and eighty degrees for so-called "spin echo" imaging, or by angles less than or equal to 90 degrees for so-called "gradient echo" imaging. In response to the applied RF pulse signals, RF coils 4 receive MR signals, i.e., signals from the excited protons within the body as they return to an equilibrium position established by the static and gradient magnetic fields. The MR signals comprising nuclear spin echo signals received by RF coils 4 as an alternating field resulting from the precessing nuclear spins, are converted into a voltage that is supplied via an amplifier 7 and multiplexer 6 to a radio-frequency receiver processing unit 8 of a radio-frequency system 22.

The radio-frequency system 22 operates in an RF signal transmission mode to excite protons and in a receiving mode to process resulting RF echo signals. In transmission mode, system 22 transmits RF pulses via transmission channel 9 to initiate nuclear magnetic resonance in volume M. Specifically, system 22 processes respective RF echo pulses associated with a pulse sequence used by system computer 20 in conjunction with sequence controller 18 to provide a digitally represented numerical sequence of complex numbers. This numerical sequence is supplied as real and imaginary parts via digital-analog converter 12 in the high-frequency system 22 and from there to a transmission channel 9. In the transmission channel 9, the pulse sequences are modulated with a radio-frequency carrier signal, having a base frequency corresponding to the resonance frequency of the nuclear spins in the measurement volume M.

The conversion from transmitting to receiving operation is done via a multiplexer 6. RF coils 4 emit RF pulses to excite nuclear proton spins in measurement volume M and acquire resultant RF echo signals. The correspondingly obtained magnetic resonance signals are demodulated in receiver processing unit 8 of RF system 22 in a phase-sensitive manner, and are converted via respective analog-digital converters 11 into a real part and an imaginary part of the measurement signal and processed by imaging computer 17. Imaging computer 17 reconstructs an image from the processed acquired RF echo pulse data. The processing of RF data, the image data and the control programs is performed under control of system computer 20. In response to predetermined pulse sequence control programs, sequence controller 18 controls generation of desired pulse sequences and corresponding scanning of k-space. In particular, sequence controller 18 controls the switching of the magnetic gradients at appropriate times, transmission of RF pulses with a determined phase and amplitude and reception of magnetic resonance signals in the form of RF echo data. Synthesizer 19 determines timing of operations of RF system 22 and sequence controller 18. The selection of appropriate control programs for generating an MR image and the display of the generated nuclear spin image is performed by a user via terminal (console) 21, which contains a keyboard and one or more screens.

System computer 20 automatically (or in response to user command entered via terminal 21) determines pulse sequence timing parameters for MR imaging with blood related signal suppression. An acquisition processor in computer 20 acquires data indicating a patient heart rate. A pulse timing processor in computer 20 automatically determines an acquisition time of an image data set readout, relative to a blood signal suppression related magnetization preparation pulse sequence, by calculating the acquisition time in response to inputs including, (a) the acquired patient heart rate, (b) data indicating a type of image contrast employed by the pulse sequence and (e) data indicating whether an anatomical signal suppression related magnetization preparation pulse sequence used has a slice selective, or non-slice selective, data acquisition readout.

Figure 4:
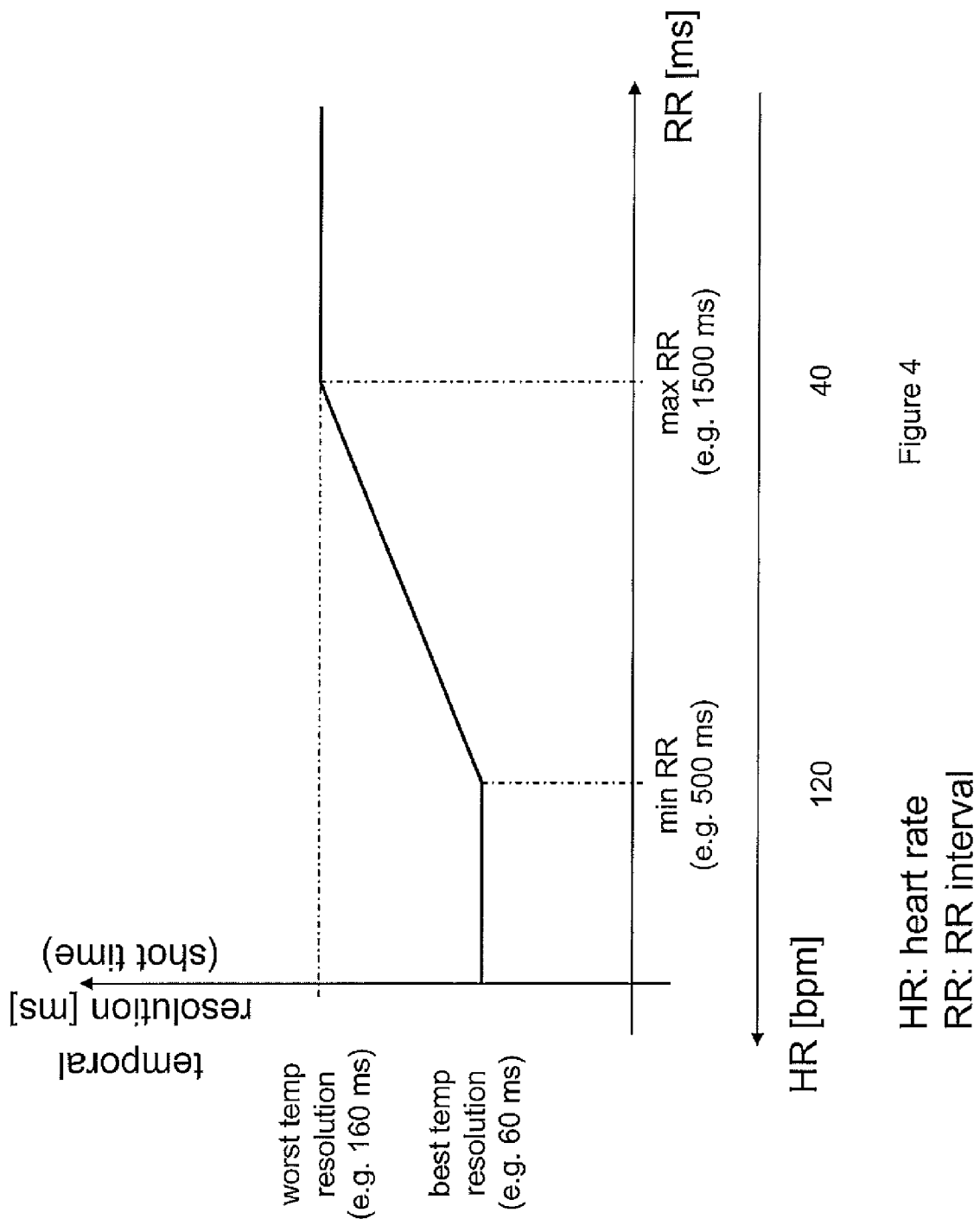
FIG. 4 shows a linear function of temporal resolution plotted against RR-wave duration and heart rate.
Figure 5:
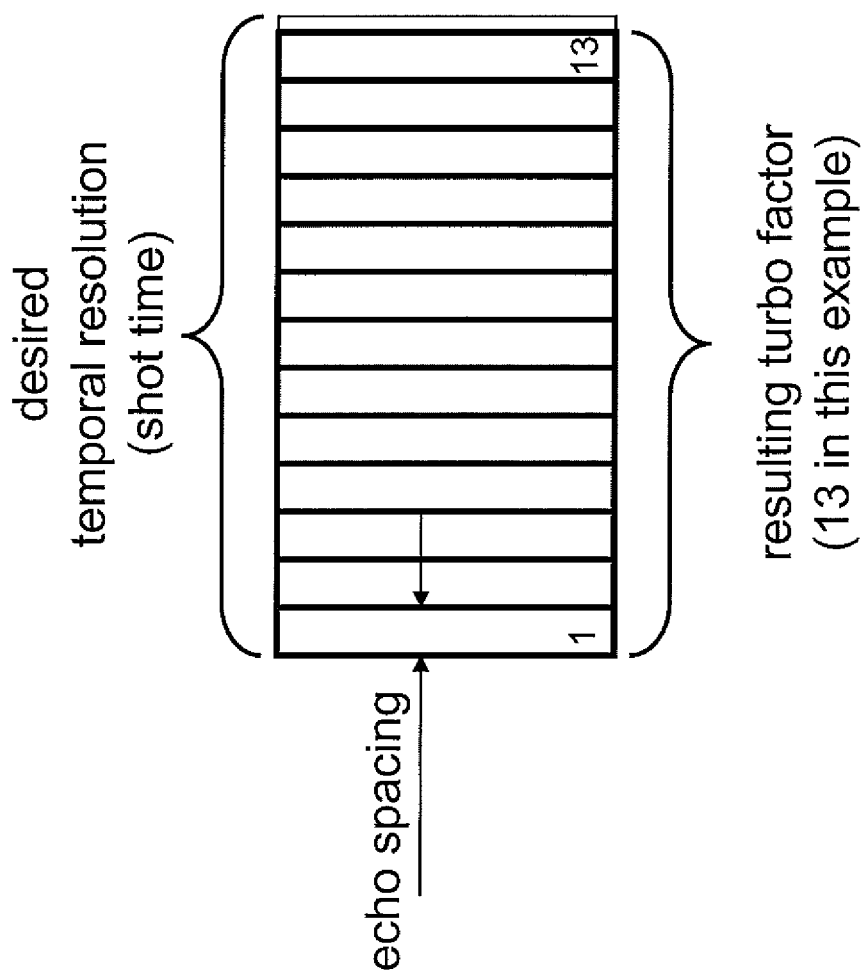
FIG. 5 shows number of echoes (read out lines of data) that fit in an obtained temporal resolution.
Figure 6:
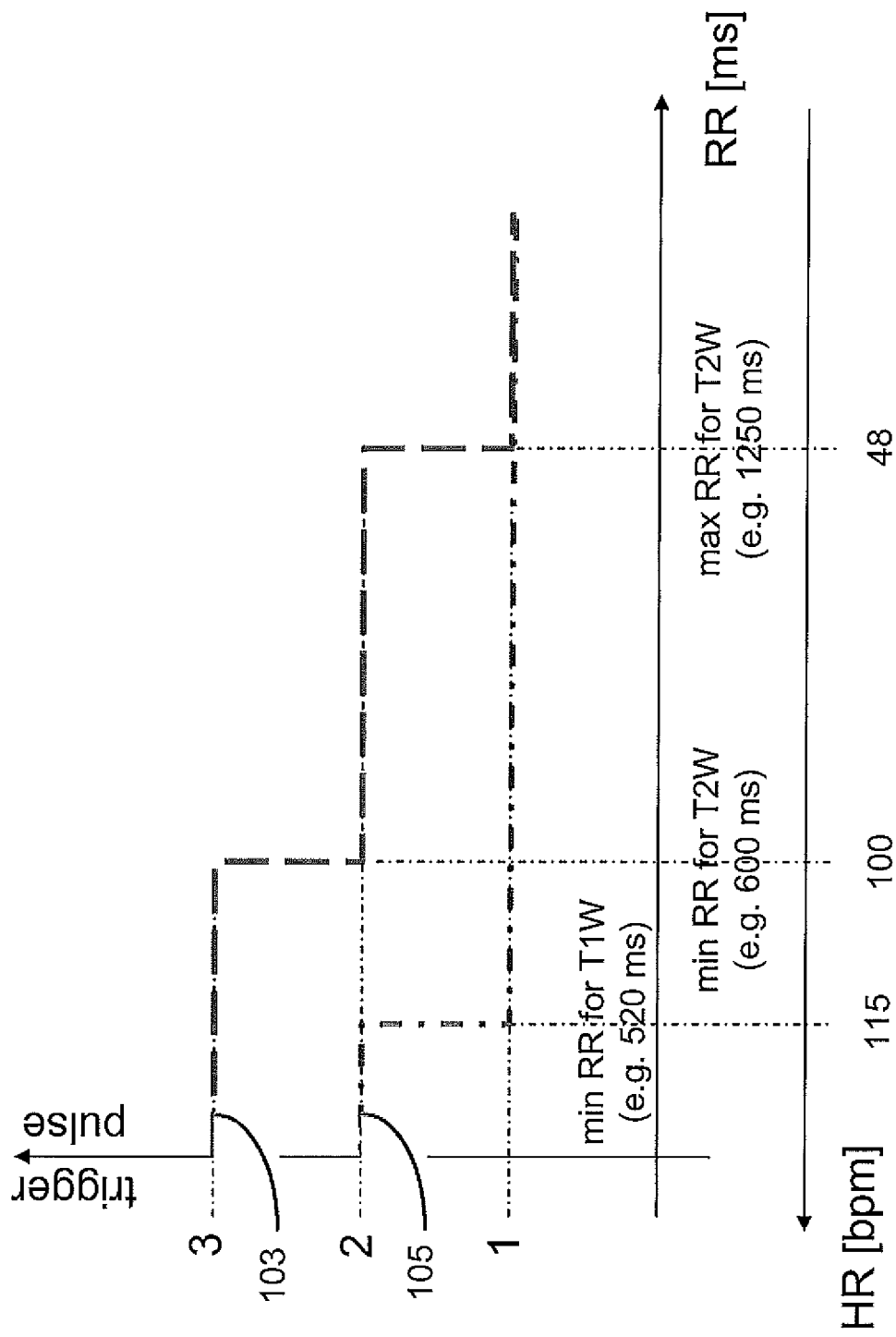
FIG. 6 adaptive selection of a trigger pulses (1, 2 or 3, y-axis) based on patient heart rate (x-axis) and RR interval (ms) and based on whether T2-weighted (T2W) imaging or T1-weighted (T1W) imaging is used, according to invention principles.
Figure 7:
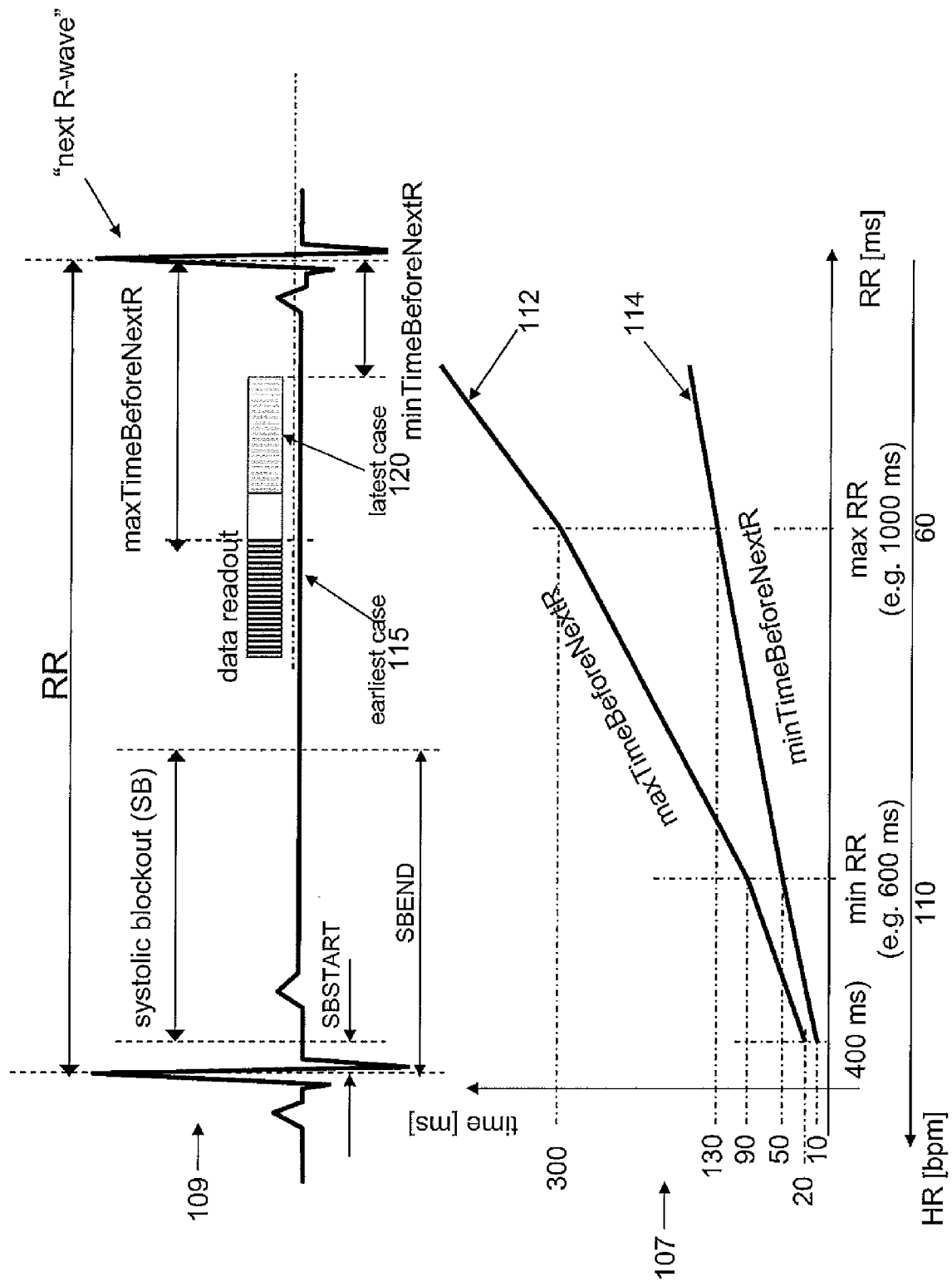
FIG. 7 shows determination of minimum and maximum allowed time between the end of the data readout and a next R-wave, according to invention principles.

System computer 20 calculates parameters as a function of a patient ECG signal RR interval, for example. System 10 in one embodiment performs steps indicated in FIGS. 4-30. System computer 20 retrieves a duration (the temporal resolution or shot time as illustrated in FIG. 4) within which data is acquired, from a look-up table or a function based on heart rate. FIG. 4 shows a linear function. Other function shapes (e.g. non-linear functions) and different numbers are usable in another embodiment. The number of echoes (read out lines of data) that fit in the obtained temporal resolution is found by dividing the temporal resolution by the echo spacing (the time between two consecutive echoes), as shown in FIG. 5. The number of echoes is called the Turbo factor or also echo train length (ETL). System computer 20 mimics selection of a trigger pulse by an experienced scanner operator by selecting an optimal value of number of echoes as a function of RR interval. System computer 20 adaptively employs different rules as illustrated in FIG. 6 for T2-weighted (T2W) imaging (line 103) and T1-weighted (T1W) imaging (line 105). Specifically, a trigger pulse of 1, 2 or 3 (y-axis) is adaptively selected based on patient heart rate (x-axis) and RR interval (ms) based on whether T2-weighted (T2W) imaging (line 103) or T1-weighted (T1W) imaging (line 105), is used.

In order to ensure that MR data is read out during the part of the cardiac cycle where the heart experiences the least amount of motion, a minimum and a maximum allowed time between the end of the data readout and a next R-wave (minTimeBeforeNextR, maxTimeBeforeNextR) are calculated as a function of the RR interval. Curves 112 and 114 for minimum and maximum allowed time are illustrated in graph 107 of FIG. 7. Different parts of curves 112 and 114 consist of linear functions (and also may comprise a constant portion in another embodiment), but other implementations with other mathematical functions are possible. Signal diagram 109 identifies where a data readout may occur in relation to a next R-wave. An earliest (black vertical pattern) readout period 115 and a latest (light grey pattern) readout period 120 are shown for a given heart rate and resulting readout duration.

Figure 8:
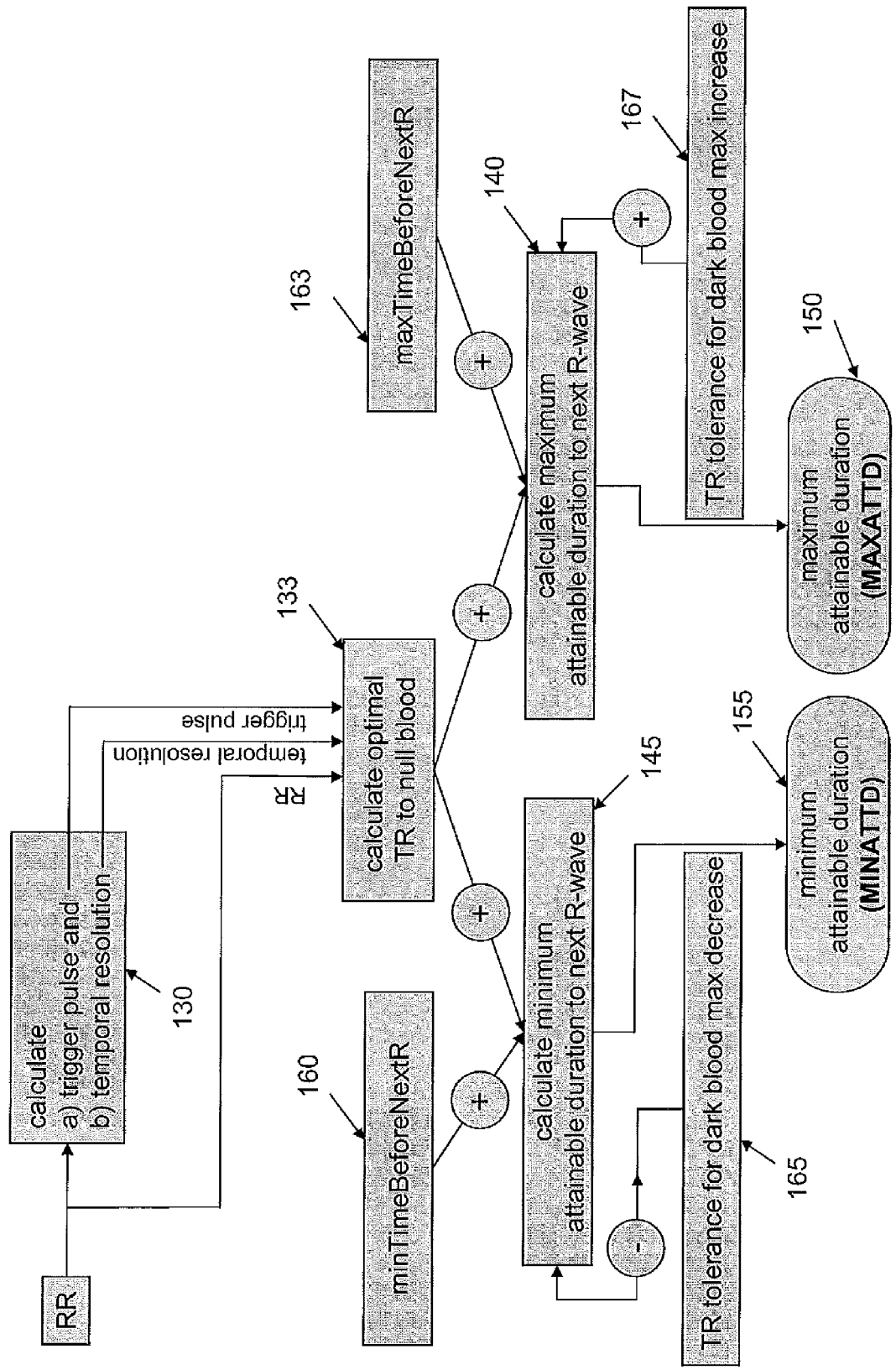
FIG. 8 shows use of a patient RR-interval to set trigger pulse and temporal resolution, according to invention principles.
Figure 9:
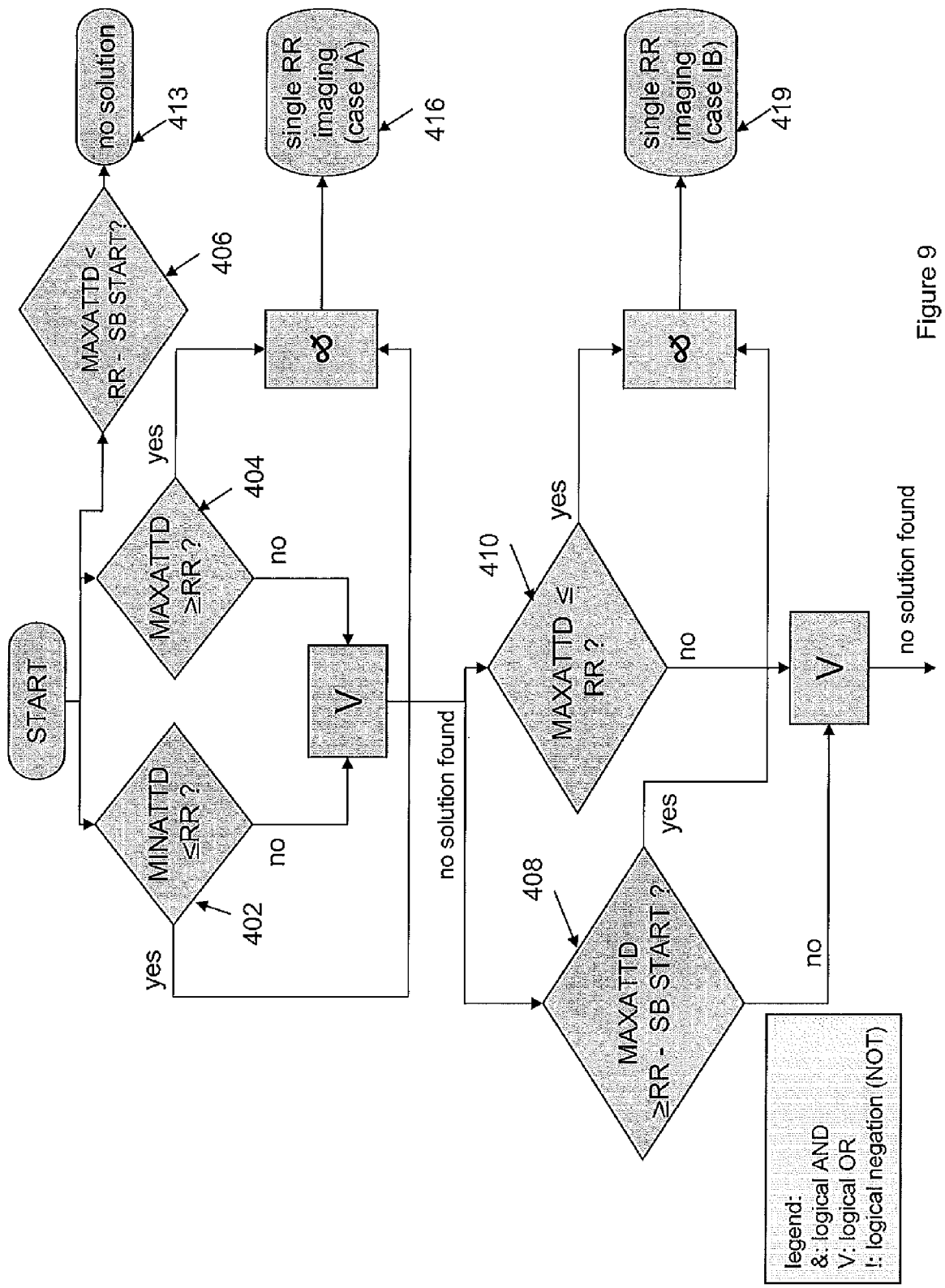
FIGS. 9-12 show a process used to determine whether single-RR, double-RR, or triple-RR time interval imaging is employed comprising the number of heart beats during which DB-preparation and readout occur, according to invention principles.

TR for optimal blood suppression is calculated as a function of the RR interval, trigger pulse, and temporal resolution. As shown in FIG. 8, a patient RR-interval is used to set trigger pulse and temporal resolution in step 130. System computer 20 (FIG. 3) in one embodiment uses formulae presented in FIGS. 21, 23, 25, 27 and 29 and determined trigger pulse and temporal resolution values to calculate an optimum TR value in step 133 to render blood dark. System computer 20 uses the optimum TR value in steps 140 and 145 to calculate the maximum (MAXATTD) 150 and the minimum (MINATTD) 155 attainable duration from the dark-blood (DB) prep to the end of the RR interval. System computer 20 uses minimum and maximum Time before next RR wave 160 and 163 respectively and TR tolerance for dark blood maximum decrease 165 and maximum increase 167 respectively in calculating the maximum (MAXATTD) 150 and the minimum (MINATTD) 155 attainable duration.

TR as used herein comprises the time from the beginning of the DB-preparation module to the end of the readout duration. Hence modifying TR effectively changes the inversion time used to null blood (which is not to be confused with the user interface parameter TI, the inversion time to null fat). FIGS. 19 to 29 illustrate the calculations and formulae used by system computer 20 (FIG. 3) to calculate an optimum TR (also termed current TR or lCurrentTR_ms) to render blood dark.

Figure 19:
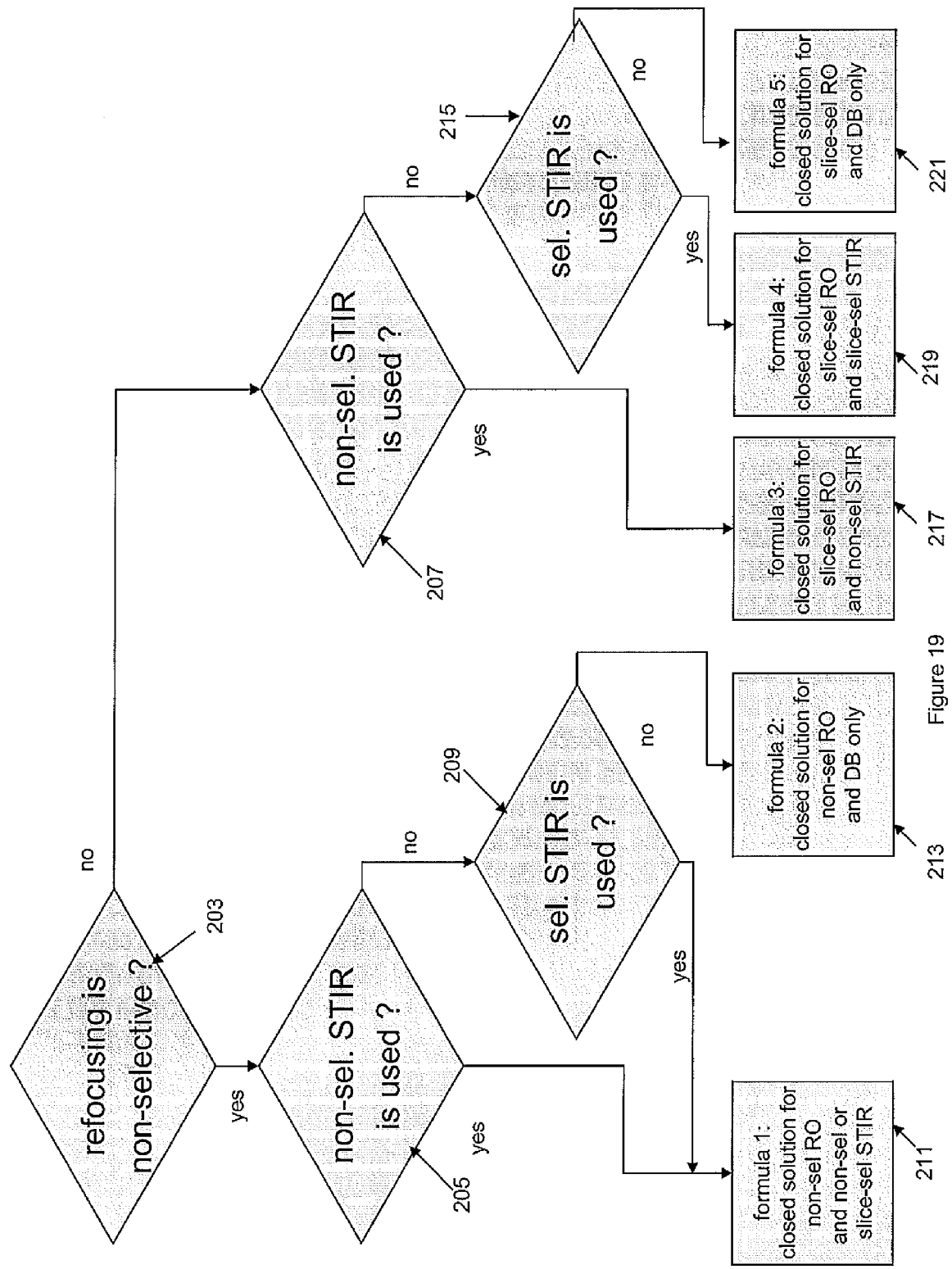
FIG. 19 shows a flow chart of a process used by a system for adaptively selecting an appropriate formula for use in calculating TR in response to multiple different inputs, according to invention principles.
Figure 20:
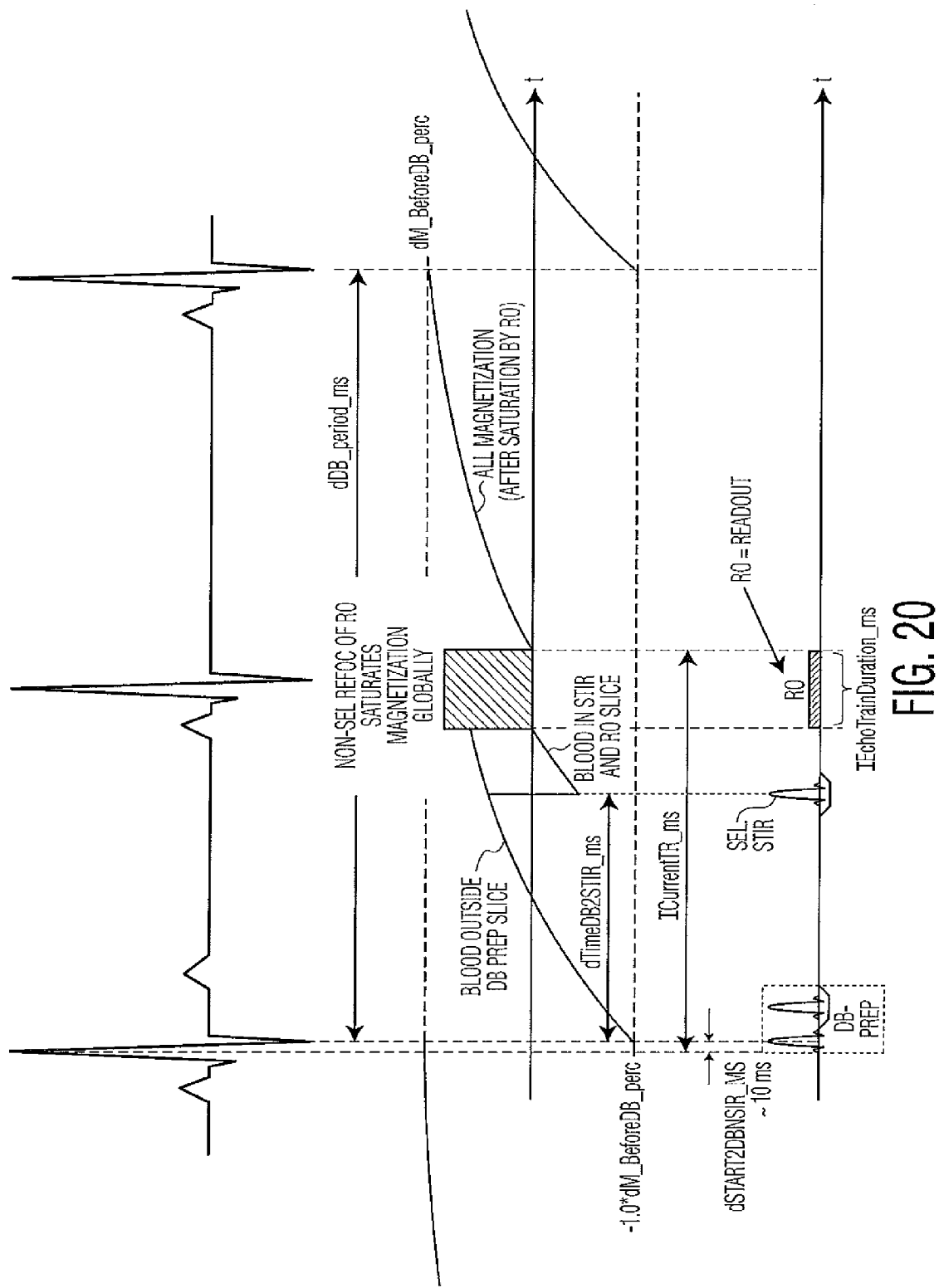
Figure 22:
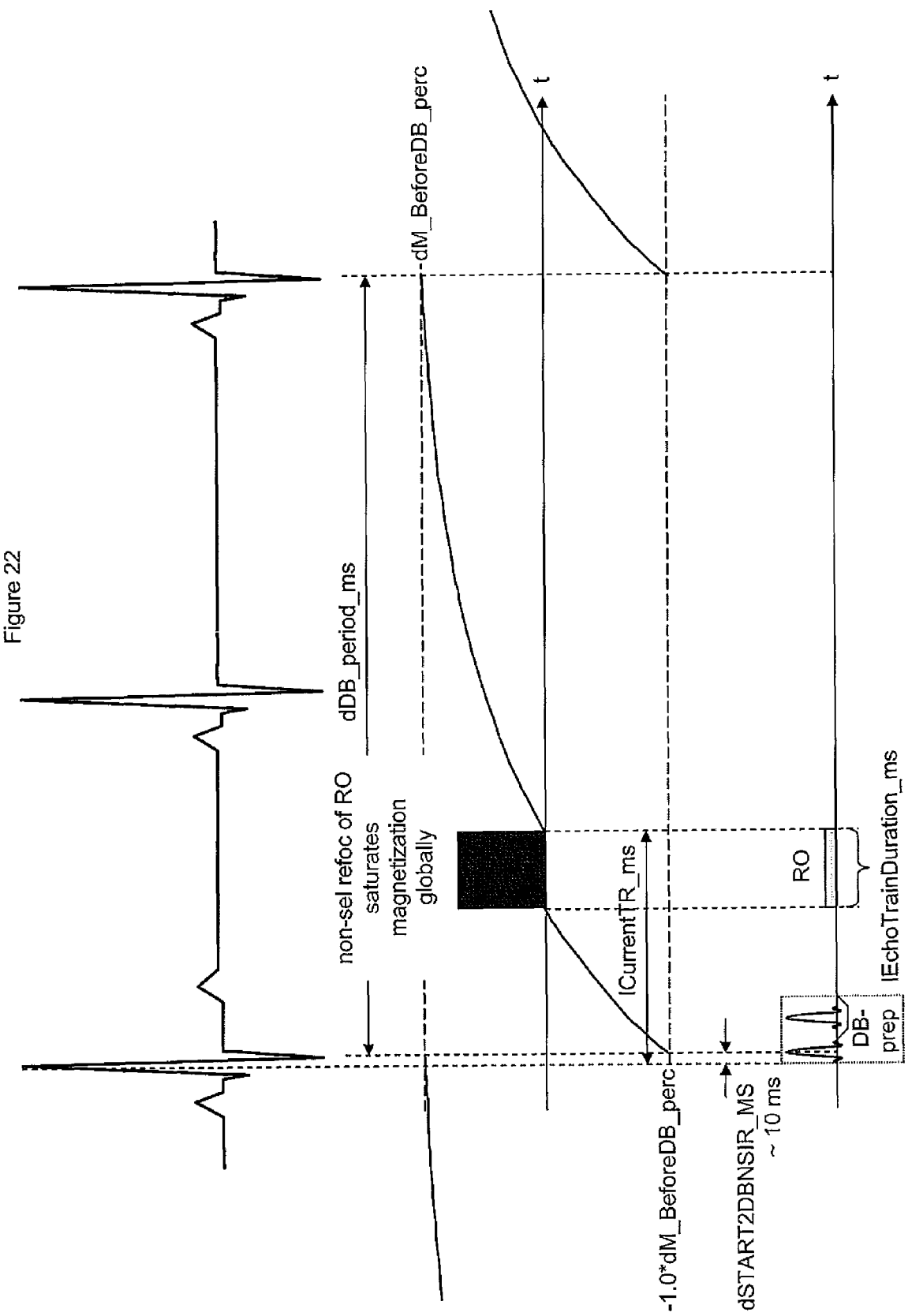
Figure 24:
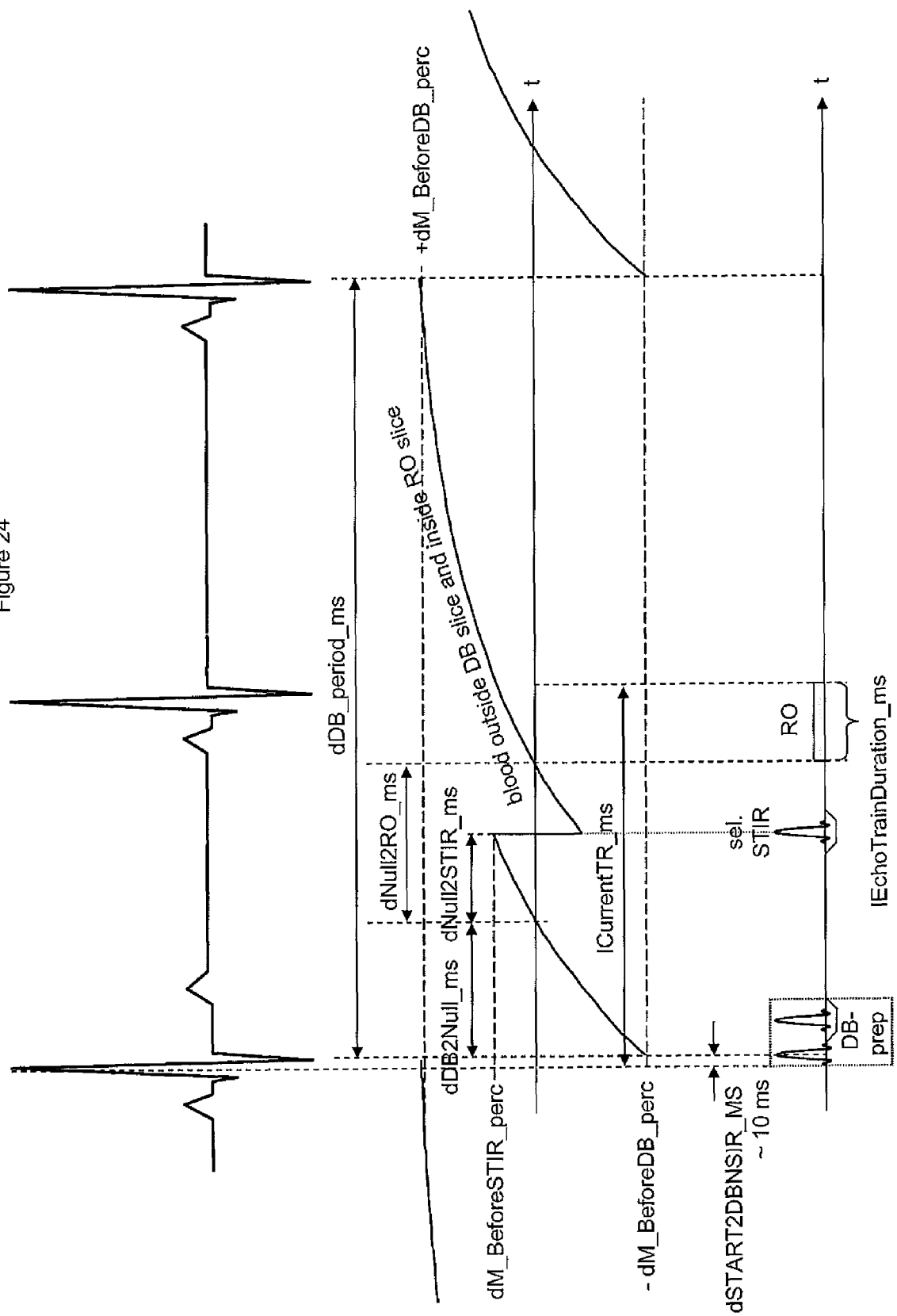
Figure 26:
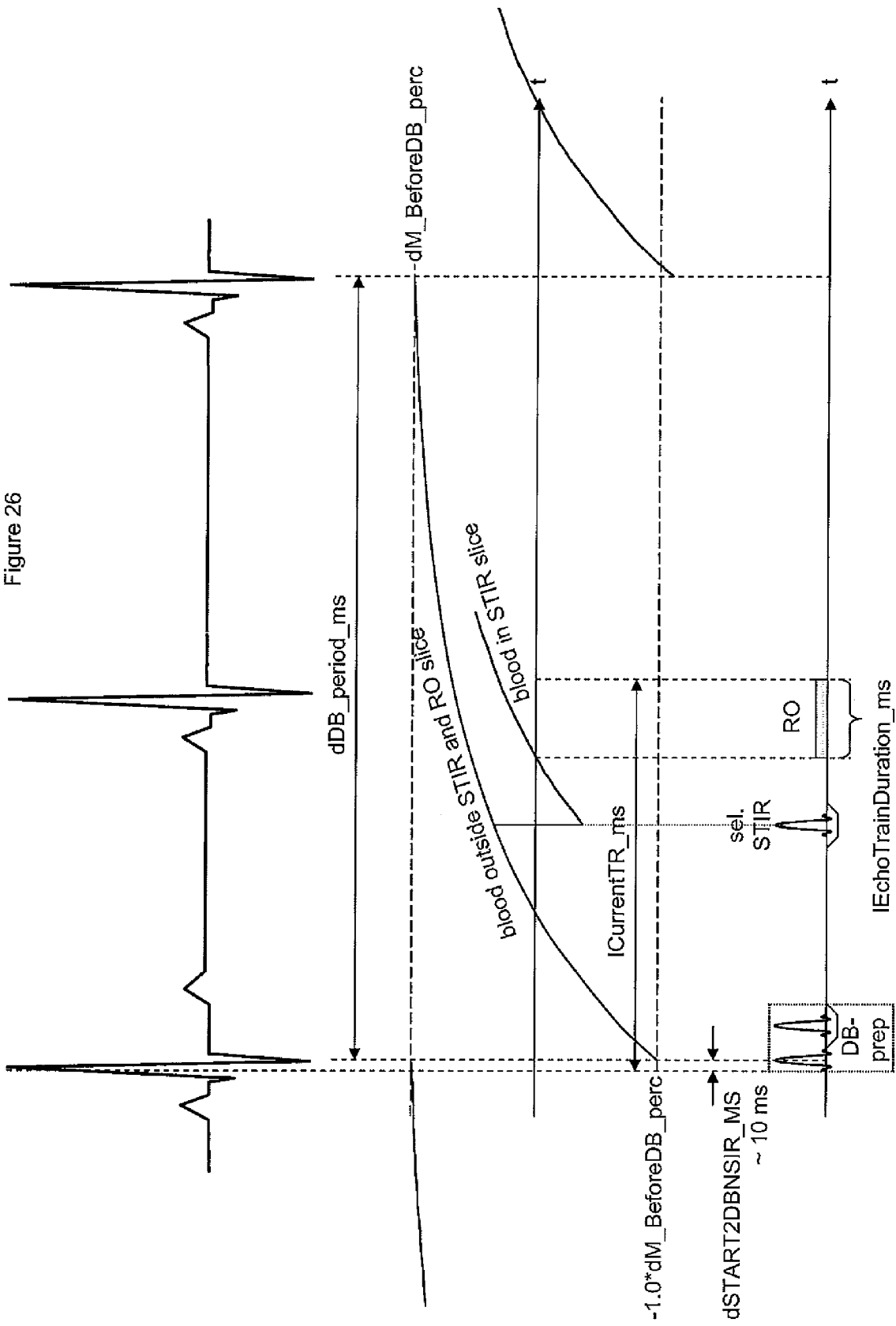
Figure 28:
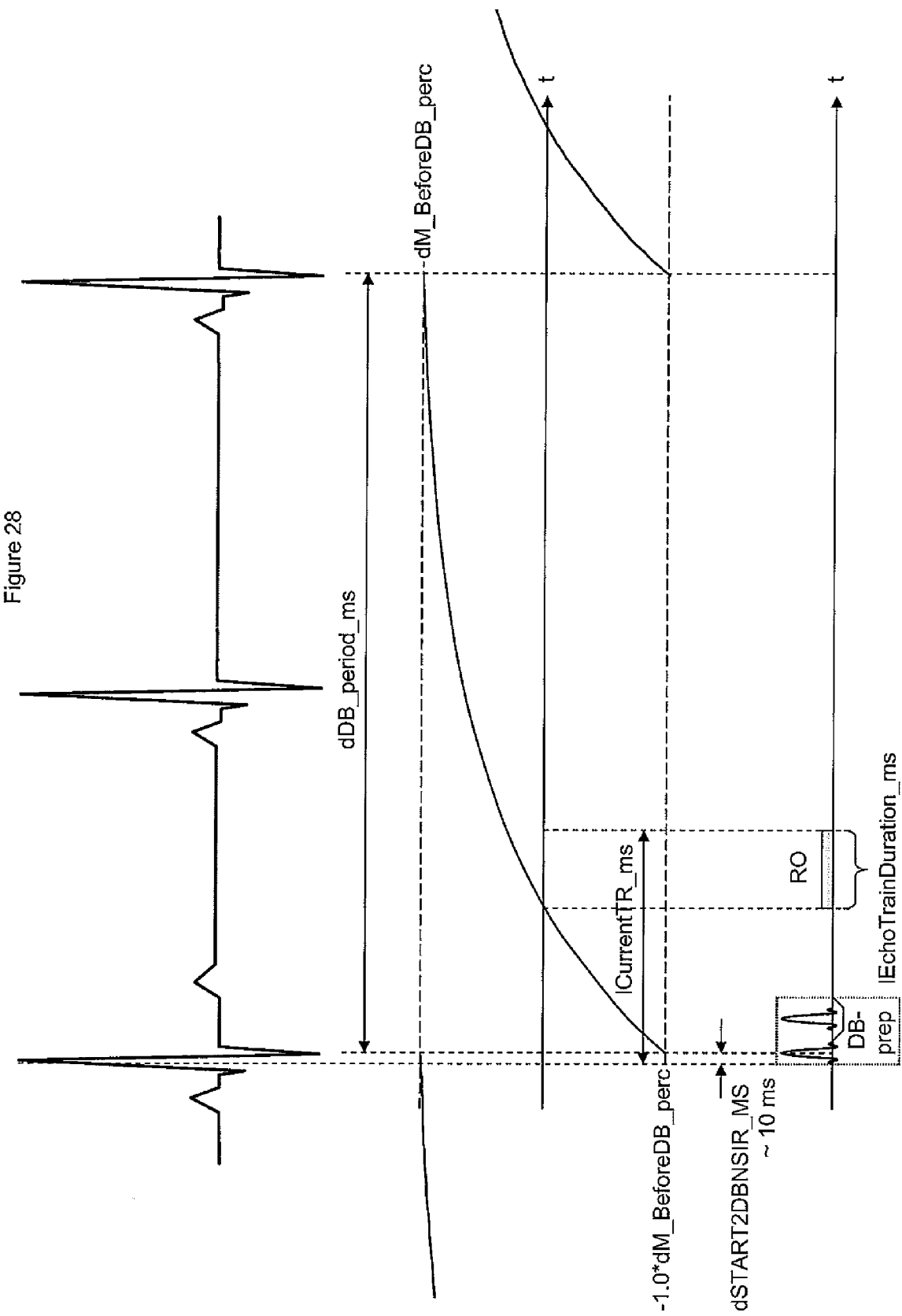

Computer 20 adaptively selects a formula to use to calculate TR in response to whether a third IR pulse (STIR pulse) is slice-selective or non-selective, and whether a data readout is realized with slice-selective or non-selective refocusing RF pulses. FIG. 19 shows a flow chart of a process used by system computer 20 for adaptively selecting an appropriate formula for use in calculating TR in response to inputs including, (a) the acquired patient heart rate, (b) data indicating a type of contrast imaging pulse sequence employed and (c) data indicating whether an anatomical signal suppression related magnetization preparation pulse sequence used has a slice selective, or non-slice selective, data acquisition readout.

In step 205 computer 20 determines whether a non-selective STIR pulse is used following determination in step 203 of that a data readout is realized with non-selective refocusing RF pulses. If it is determined in step 205 that a non-selective STIR pulse is used or it is determined in step 209 that a selective STIR pulse is used, Formula 1 is employed in step 211 for calculating TR (lCurrentTR in the formulas). Formula 1 is shown in FIG. 21 with corresponding pulse sequence characteristics shown in FIG. 20. Formula 1 is used for non-slice-selective refocusing RF pulses of a readout pulse sequence and non-selective or slice-selective STIR preparation. Formula 1 assumes that blood (inside and outside a STIR slice) is saturated following non-selective refocusing RF pulses. In the case that a slice-selective STIR pulse is used, computer 20 assumes that blood inverted by the STIR pulse has not left the slice during readout (RO) and a thick STIR slice is used. Therefore, Formula 1 is employed for calculation of TR for non-selective readout with slice-selective or non-selective STIR. If it is determined in step 209 that a selective STIR pulse is not used, Formula 2 is employed for calculating TR. Formula 2 is applied in step 213 to calculate TR in response to use of non-selective refocusing RF pulses and a Dark-Blood Turbo-Spin Echo (TSE) pulse sequence. Formula 2 applies to non-selective refocusing RF pulses and DB-preparation (not STIR). Formula 2 is shown in FIG. 23 with corresponding pulse sequence characteristics shown in FIG. 22.

In step 207 computer 20 determines whether a non-selective STIR pulse is used following determination in step 203 that a data readout is realized with slice-selective refocusing RF pulses. If it is determined in step 207 that a non-selective STIR pulse is used, Formula 3 is employed in step 217 for calculating TR. The formula assumes that the blood inverted by the STIR pulse has not left the slice during readout. Formula 3 is used in case of slice-selective refocusing RF pulses and non-selective STIR. Specifically, Formula 3 is employed for calculation of TR for slice selective readout with use of a non-selective STIR pulse. Formula 3 is shown in FIG. 25 with corresponding pulse sequence characteristics shown in FIG. 24.

If it is determined in step 215 that a selective STIR pulse is used following determination in step 207 that a non-selective STIR pulse is not used, Formula 4 is employed by computer 20 in step 219 for calculating TR. Formula 4 is used to determine TR if slice-selective refocusing RF pulses and slice-selective STIR are used. Formula 4 is shown in FIG. 27 with corresponding pulse sequence characteristics shown in FIG. 26. Formula 4 assumes that the blood inverted by the STIR pulse has not left the slice during RO. If it is determined in step 215 that a selective STIR pulse is not used following determination in step 207 that a non-selective STIR pulse is also not used, Formula 5 is employed by computer 20 in step 221 for calculating TR. Formula 5 applies to slice-selective refocusing RF pulses and DB-preparation (not STIR). Formula 5 is shown in FIG. 29 with corresponding pulse sequence characteristics shown in FIG. 28. Specifically, Formula 5 is employed for calculation of TR for slice selective readout with use of a Dark-Blood Turbo-Spin Echo (TSE) pulse sequence. Formulas 1-5 provide closed solutions to determining optimum timing. The system in other embodiments performs iterative calculation.

Variables used in FIGS. 19-29 are as follows.

dTimeDB2STIR_ms: the time from the center of the non-selective IR pulse of the DB-preparation module to the center of the STIR pulse (milliseconds)

dSTART2DBNSIR_MS: the time from the beginning of the DB-preparation module to the non-selective IR pulse of the module (milliseconds)

dDB_period_ms: the trigger pulse times the RR (milliseconds)

lEchoTrainDuration_ms: the shot time or temporal resolution (milliseconds)

dDB2Null_ms: the time from the center of the non-selective IR pulse of the DB-preparation module to the null point of blood (milliseconds)

dNull2STIR_ms: the time from the null point of blood to the center of the STIR pulse (milliseconds)

dNull2RO_ms: the time from the null point of blood to the beginning of the data readout (milliseconds)

dM_BeforeDB_perc: the magnetization of blood immediately before the application of the non-selective IR pulse of the DB-preparation module (percent of M0).

In another embodiment, computer 20 iteratively determines TR. specifically, computer 20 determines the maximum (MAXATTD) and minimum (MINATTD) attainable duration from the beginning of DB-preparation to the next R-wave (not to the end of the readout). Computer 20 determines MAXATTD and MINATTD values as shown in FIG. 8 using a calculated optimal TR value determined using the process of FIG. 19, minTimeBeforeNextR value and maxTimeBeforeNextR value as well as the two parameters "TR tolerance for dark blood max decrease" and "TR tolerance for dark blood max increase". The latter two parameters specify the allowed deviation from the optimal TR value so that the DB-preparation and data readout occur in appropriate parts of a cardiac cycle without visibly compromising blood signal nulling.

In response to determining the optimal timing for rendering blood black (lCurrentTR in the formulas), system 10 employs a process shown in the flowchart of FIGS. 9-12 to select whether the timing fits in a 1, 2 or 3 heart cycles and where within a heart cycle DB-preparation is to be placed to achieve optimal image quality. System 10 optimizes black blood timing and optimizes the timing (i.e. the position of the DB-preparation and of the readout within the RR interval) to ensure the least amount of cardiac motion during readout (least "camera shake") and the largest amount of blood exchange between DB-preparation and readout without which DB-preparation does not work. The readout is not limited to Turbo-Spin Echo (TSE) type.

System 10 automatically sets scan parameters for dark blood imaging in the heart whereby the heart rate of the subject which is a determinant of the time between repetitions of the dark blood preparation pulse, is used as an input together with the desired image contrast type, (e.g. T1, T2 or STIR) and whether selective or non-selective inversion is to be used to determine the correct timing of the time between the dark-blood preparation and the data acquisition. System 10 uses patient heart rate to determine the maximum acceptable duration of data acquisition during the heart beat to mitigate negative effects on image quality of heart motion. The timing computation is adaptively varied in response to whether or not an inversion pulse used is either selective or non-selective.

Figure 10:
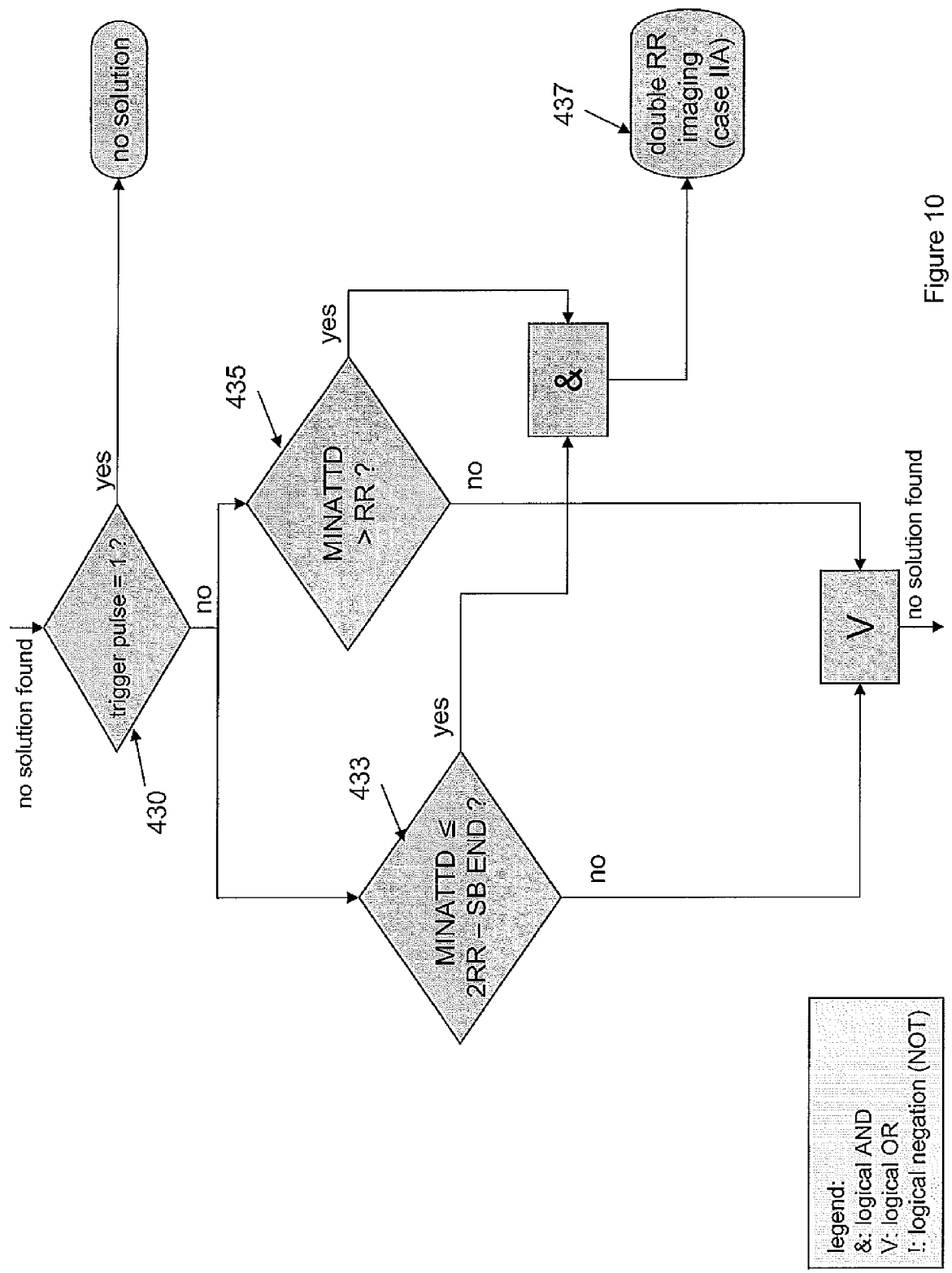
Figure 11:
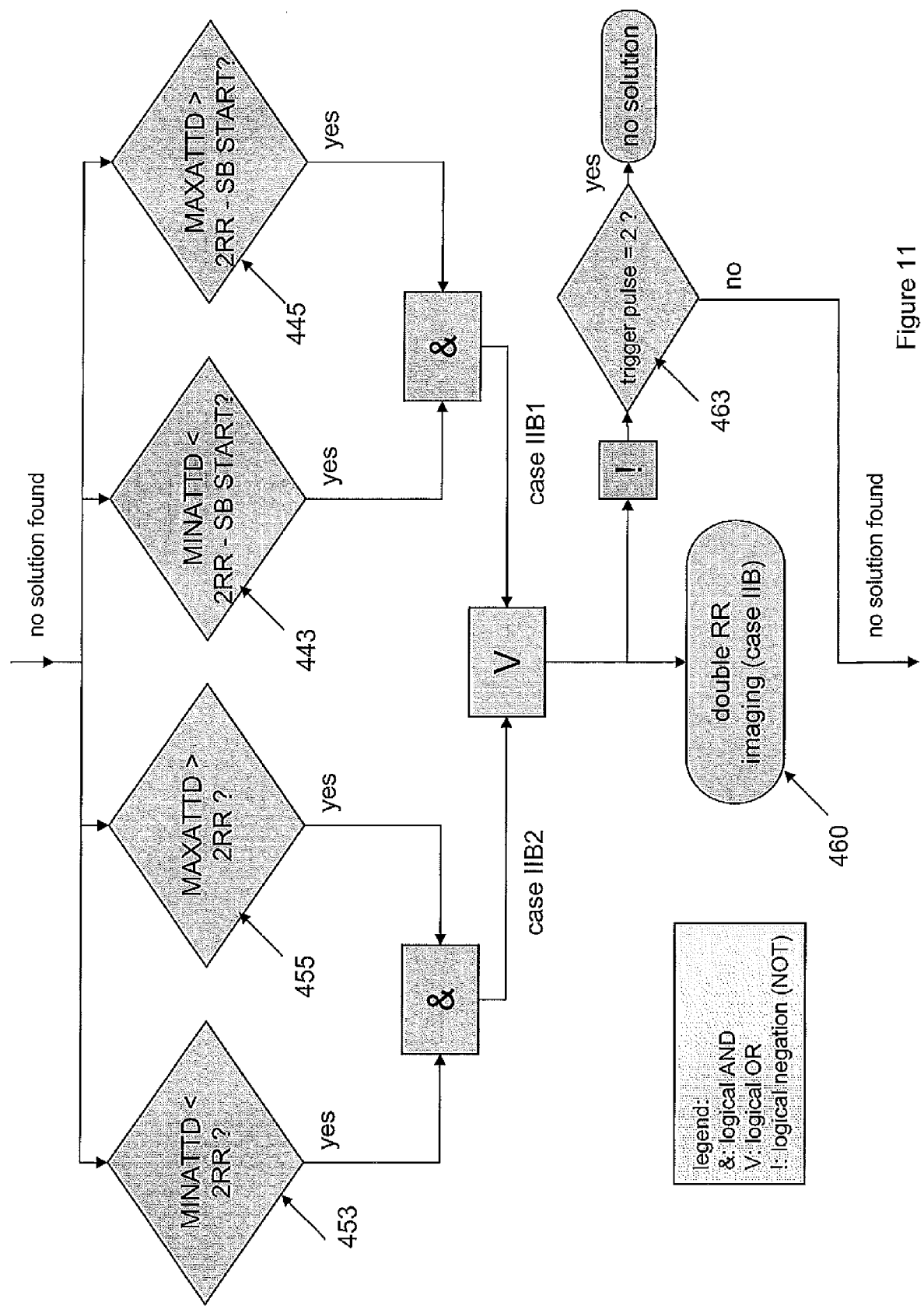
Figure 12:
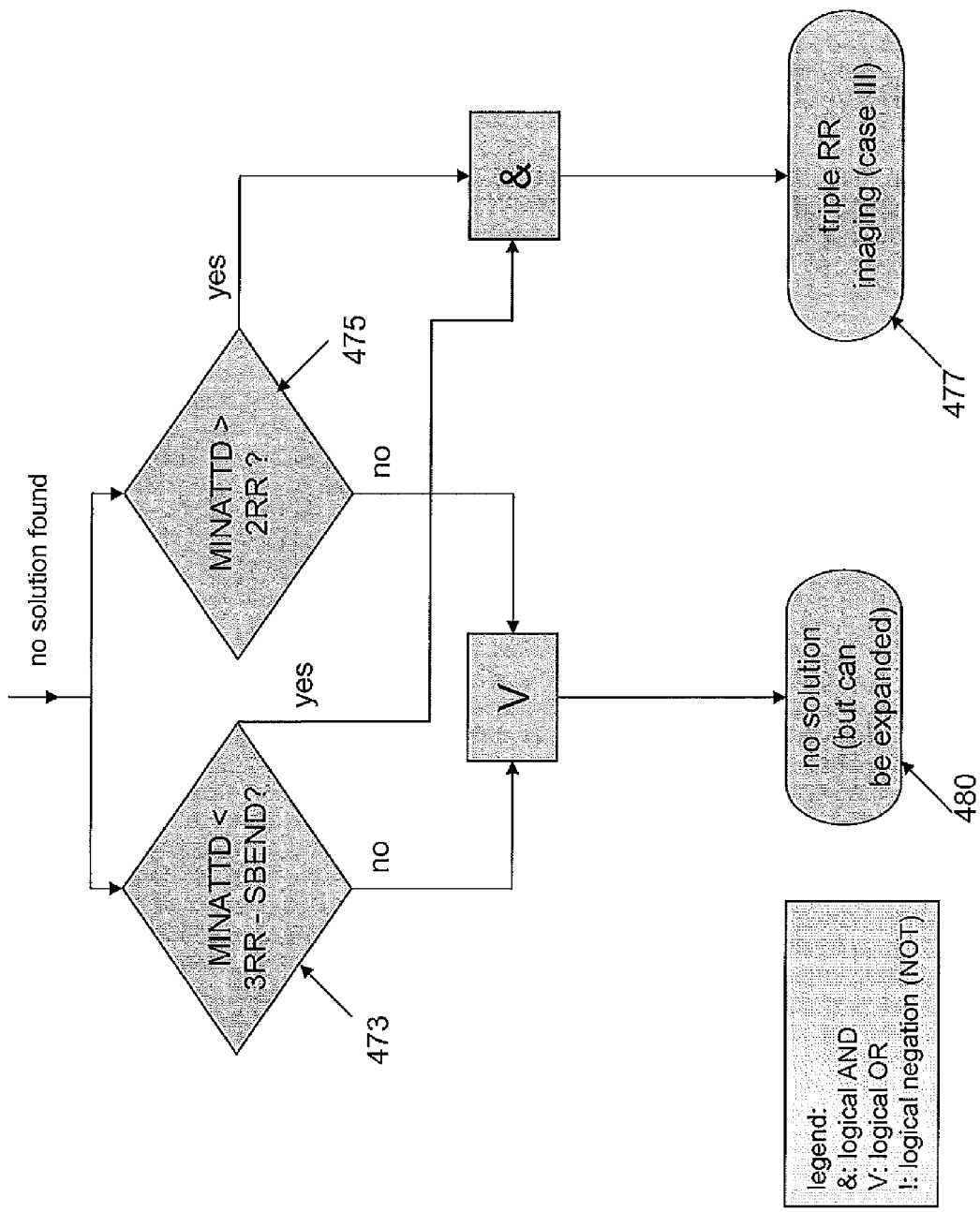
Figure 13:
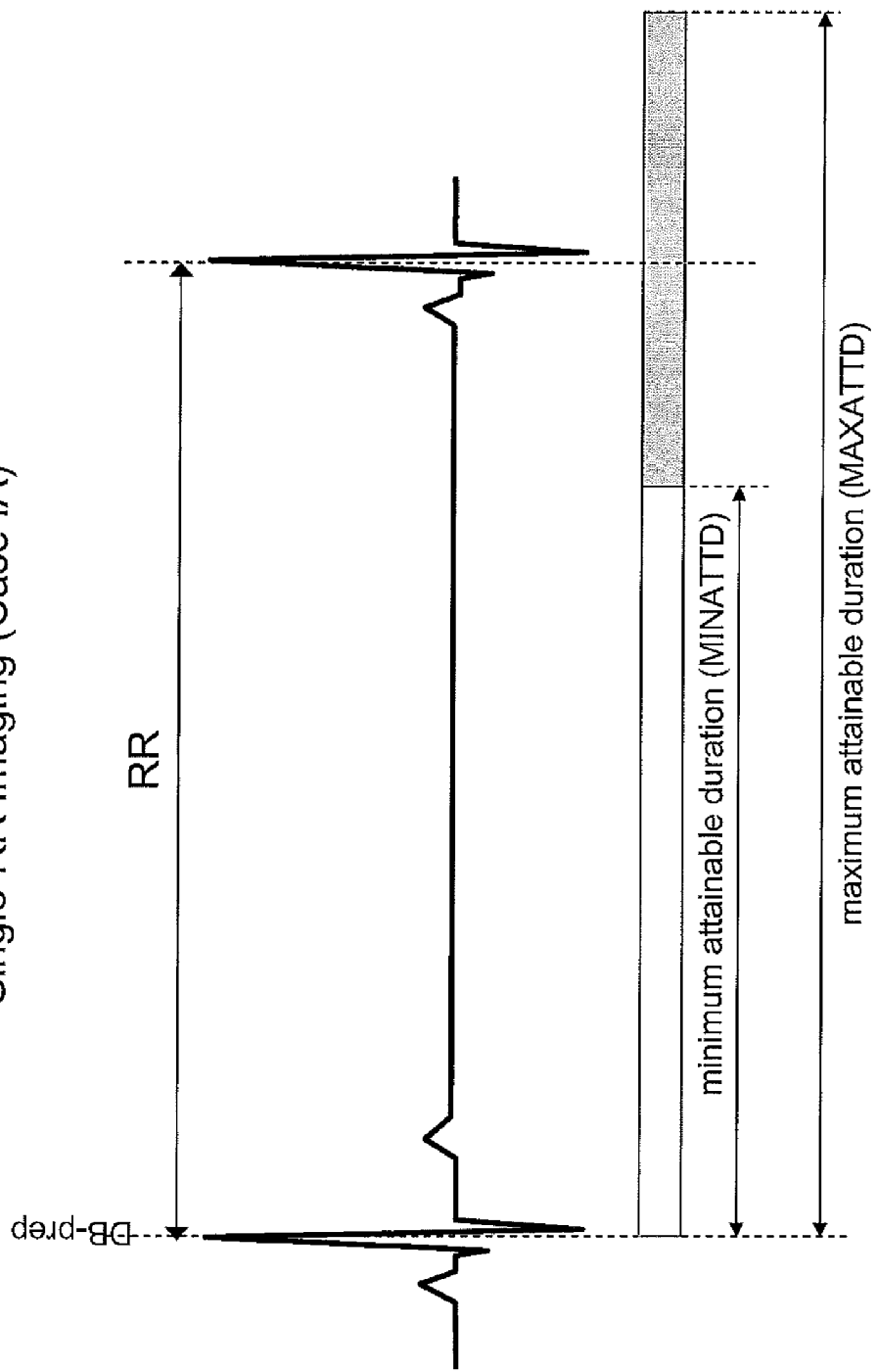
FIG. 13-17 show pulse sequence timing characteristics associated with single-RR, double-RR, or triple-RR time interval imaging, according to invention principles.
Figure 14:
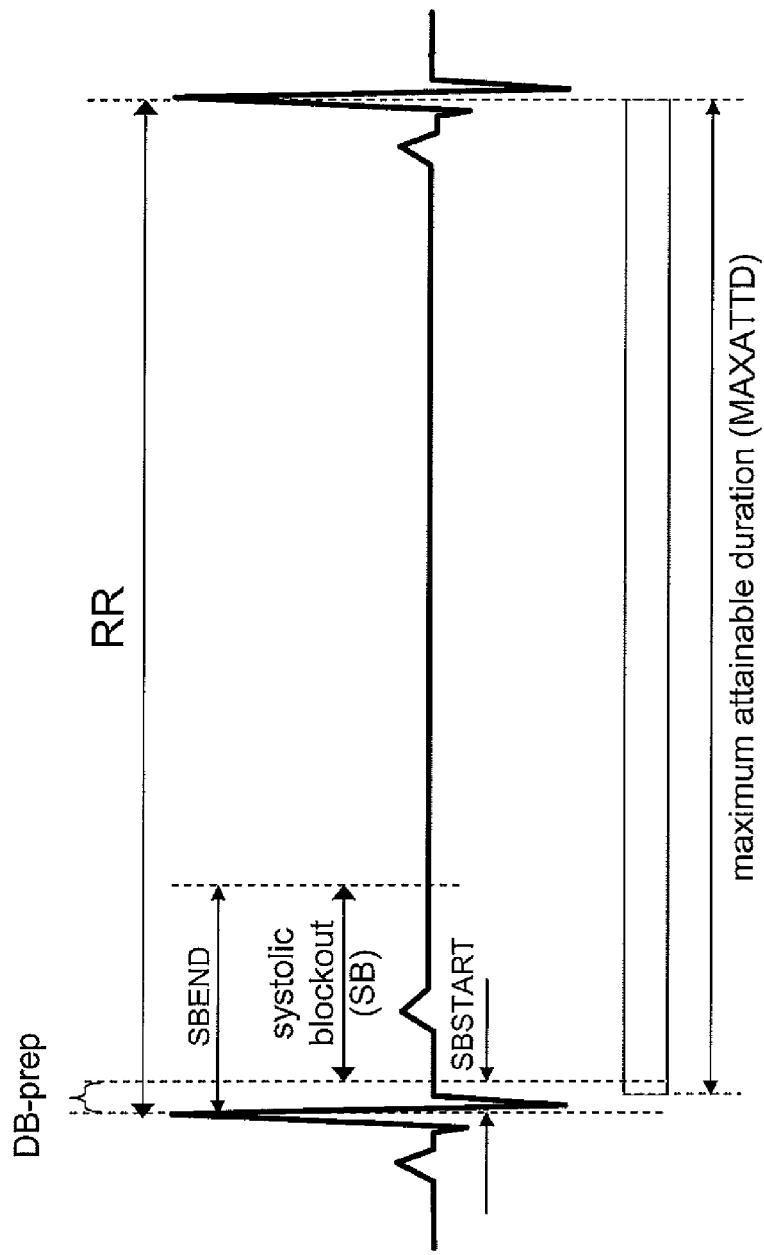

System computer 20 employs the process shown in the flowchart of FIGS. 9-12 to determine whether single-RR, double-RR, or triple-RR time interval imaging is employed comprising the number of heart beats during which DB-preparation and readout occur. Computer 20 employs the process of the flowchart of FIG. 9 using the calculated minimum (MINATTD) and maximum (MAXATTD) attainable duration values to determine whether DB prep and readout fit in a single heartbeat with prep at the R-wave (case IA) or up to SB START (Systolic Blockout Start) after the R-wave (case IB). If neither works, the process of the flowchart of FIG. 10 is employed. Following the start if it is determined in step 406 that MAXATTD is less than the interval RR to SB START, computer 20 determines no solution exists 413. Two cases exist in single-RR imaging. In case IA if MINATTD is less than or equal to RR and MAXATTD is greater than or equal to RR, a DB-preparation pulse is initiated at the R-wave and readout occurs during a diastolic phase of the same heart cycle as illustrated in FIG. 13. If MINATTD is not less than or equal to RR or MAXATTD is not greater than or equal to RR and (MAXATTD is greater than or equal to RR-SBSTART and MAXATTD is less than or equal to RR), a DB-preparation pulse is initiated after an R-wave up to a following SB START and readout occurs during a diastolic phase of the same heart cycle (case IB) as illustrated in FIG. 14. Otherwise the process of FIG. 10 is performed.

Computer 20 employs the process of the flowchart of FIGS. 10 and 11 using the MINATTD and MAXATTD attainable duration values to determine whether DB prep and readout fit in two heartbeats with diastolic DB-prep in the first RR and readout in the second RR interval. If not, the process of FIG. 12 is employed. For double-RR imaging two cases exist in which the DB-preparation module is initiated either in a diastolic phase of the first RR (case IIA: diastolic prep) or just after the R-wave of the first RR (case IIB: DB-preparation right after R-wave). Note that the terms single-, double- and triple-RR imaging refer to the number of heart beats during which DB-preparation and readout occur. If computer 20 determines in step 430 that a trigger pulse is 1 there is no double RR imaging solution. This is unrelated to the trigger pulse determined in FIG. 6, e.g., double-RR imaging may be used yet it is only gated every third RR-wave. For double-RR imaging computer 20 requires at least a trigger pulse of 2. This is unlikely to happen in practice as parameters are chosen to avoid such a scenario.

Figure 15:
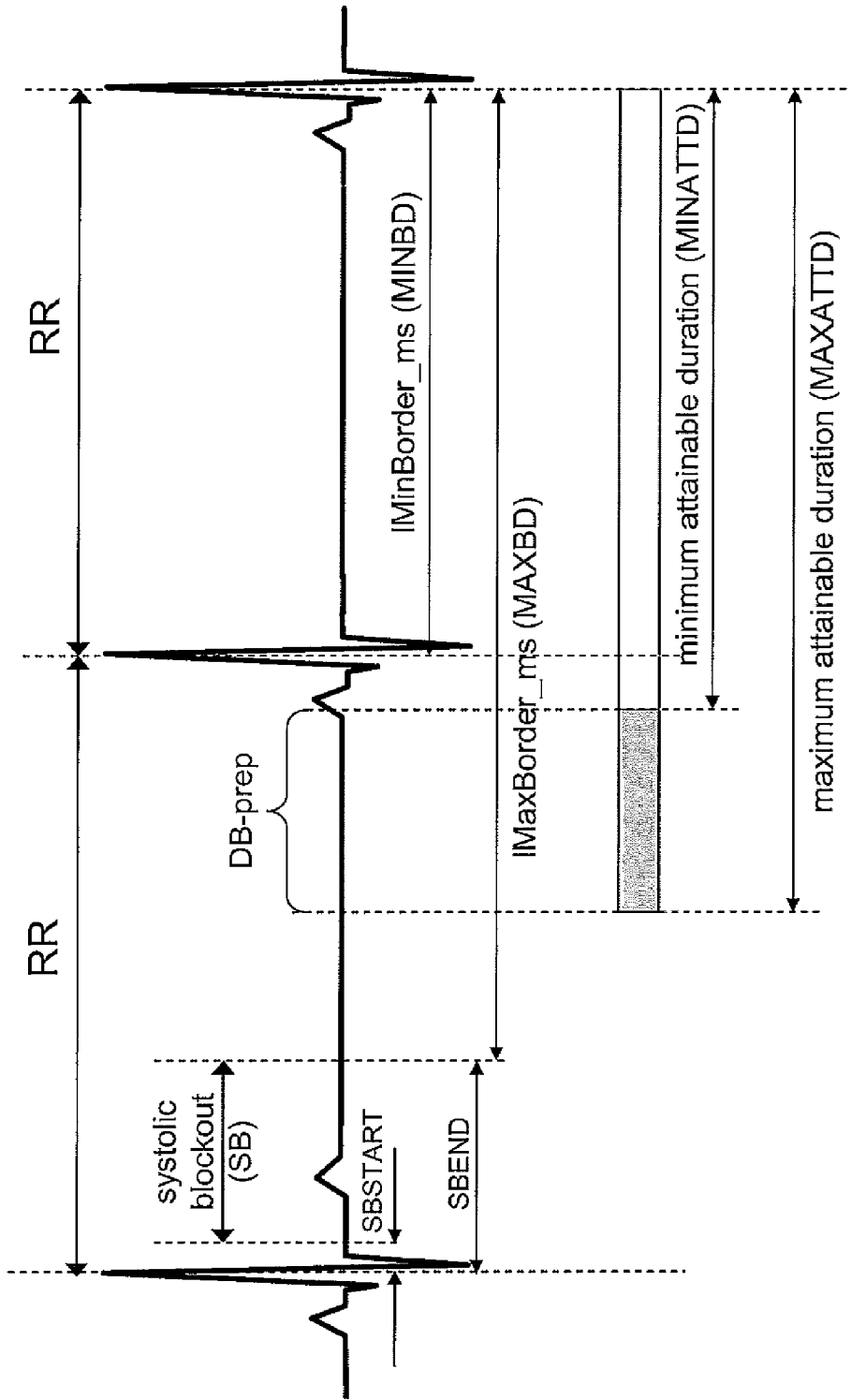

In FIG. 10 computer 20 performs steps 433 and 435, if MINATTD is less than or equal to 2RR-SB END and MINATTD is greater than RR, double RR imaging (case IIA) is performed as illustrated in FIG. 15, otherwise there is no solution and the process of FIG. 11 is performed. FIG. 15 indicates DB-prep occurs in a diastolic phase of a first heart cycle and readout occurs in a diastolic phase of a successive second heart cycle. SB START and SB END are the start and the end of the systolic block out period. During this period, neither DB-preparation nor readout are performed to prevent mis-registration between the DB-preparation slab and the readout slice.

Figure 16:
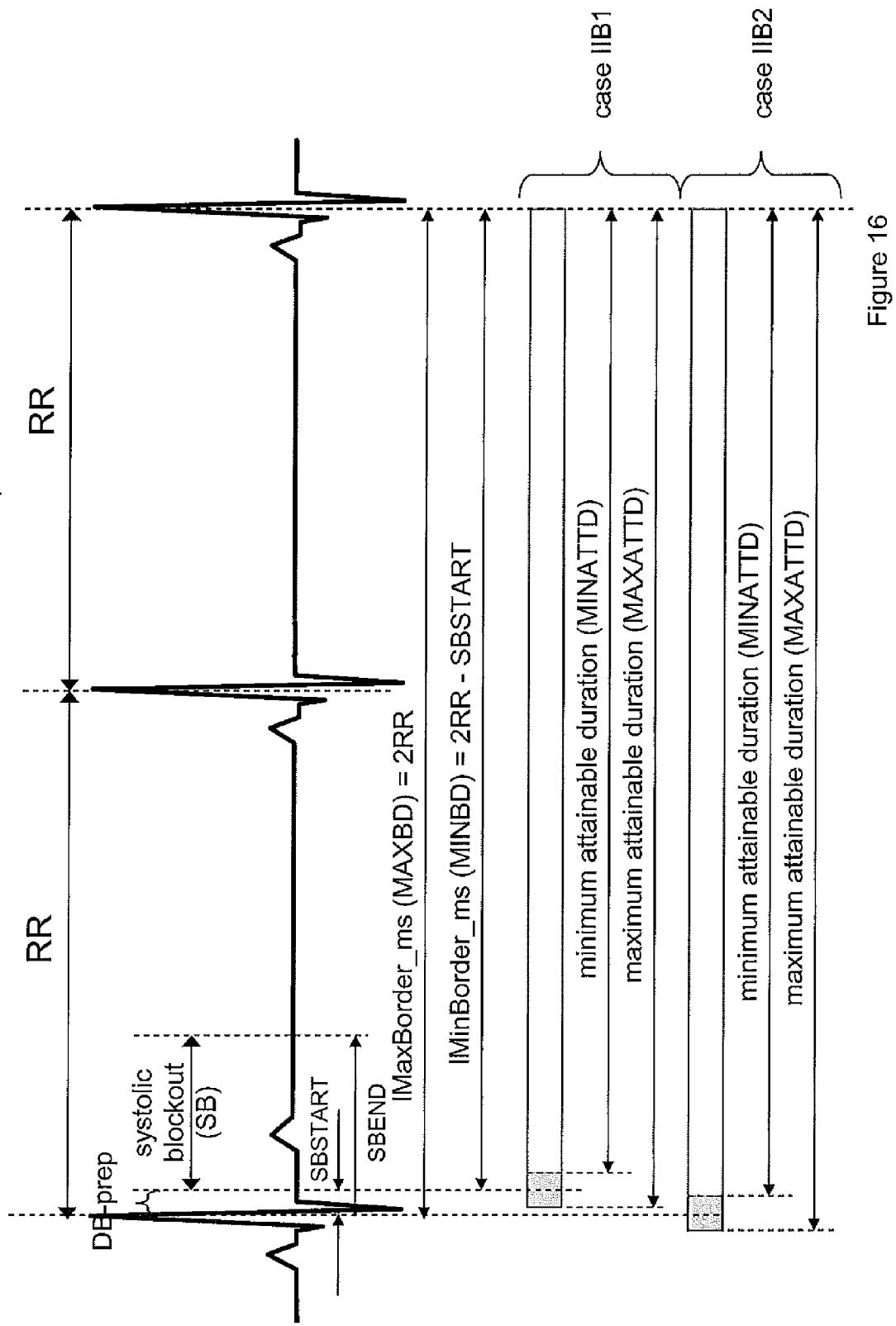

In FIG. 11 computer 20 performs steps 443 and 445, if MINATTD is less than 2RR-SB START and MAXATTD is greater than 2RR-SB START, double RR imaging (case JIB) is performed in step 460 as illustrated in FIG. 16. Similarly, in steps 453 and 455, if MINATTD is less than 2RR and MAXATTD is greater than 2RR, double RR imaging (case IIB) is also performed in step 460 as illustrated in FIG. 16. However if computer 20 determines in step 463 that the trigger pulse is not 2 there is no solution and the process of FIG. 12 is performed. FIG. 16 indicates DB-prep occurs between an R-wave of the first heart cycle and up to SBSTART thereafter and the readout occurs in a diastolic phase of a successive second heart cycle.

Figure 17:
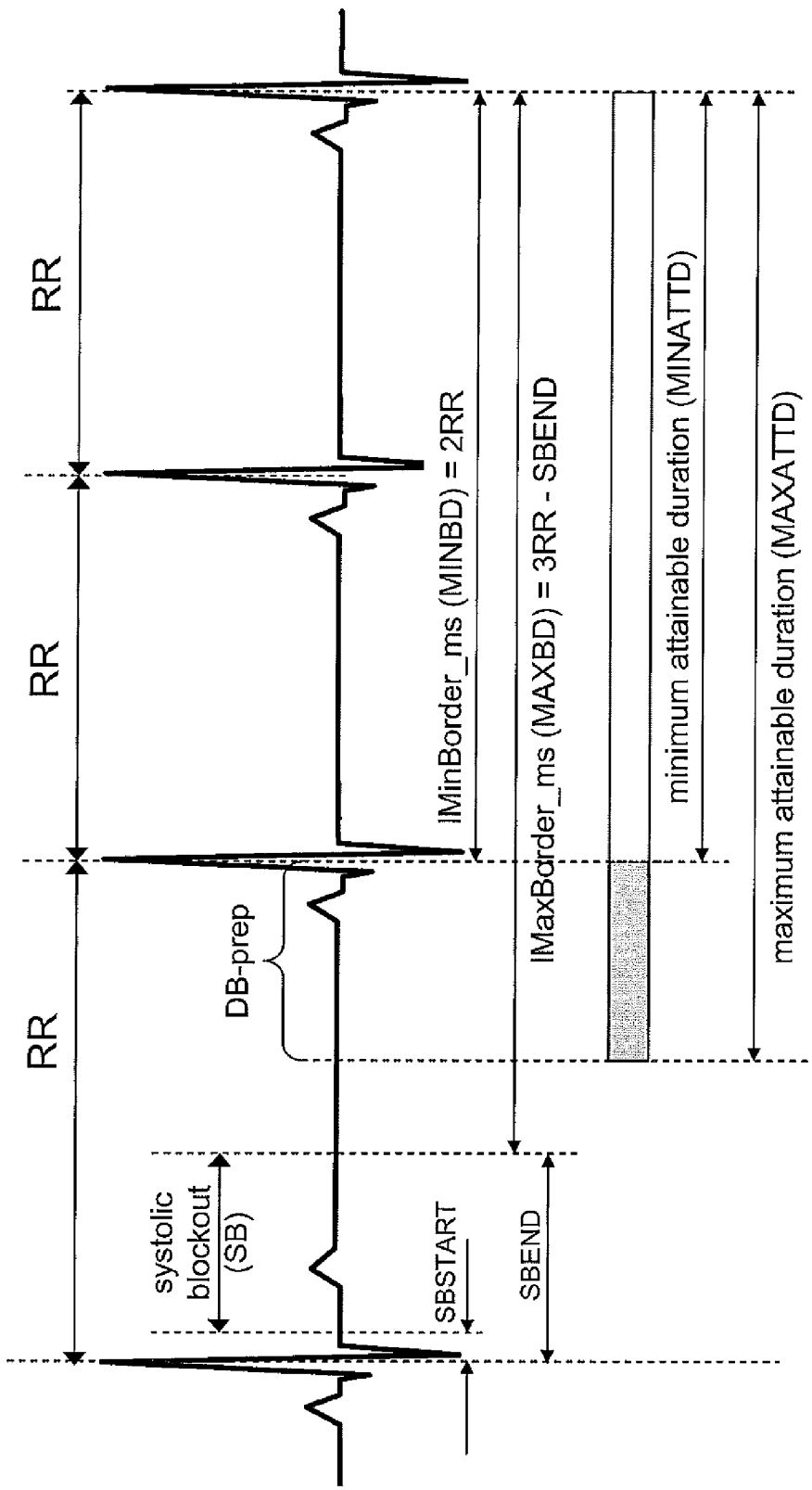

In FIG. 12 computer 20 performs steps 473 and 475, if MINATTD is less than 3RR-SB END and MINATTD is greater than 2RR, triple RR imaging (case III) is performed in step 477 as illustrated in FIG. 17, otherwise no solution is determined in step 480. FIG. 17 indicates the DB-prep occurs in the diastolic phase of a first heart cycle and the readout occurs in the diastolic phase of the third heart cycle.

Figure 18:
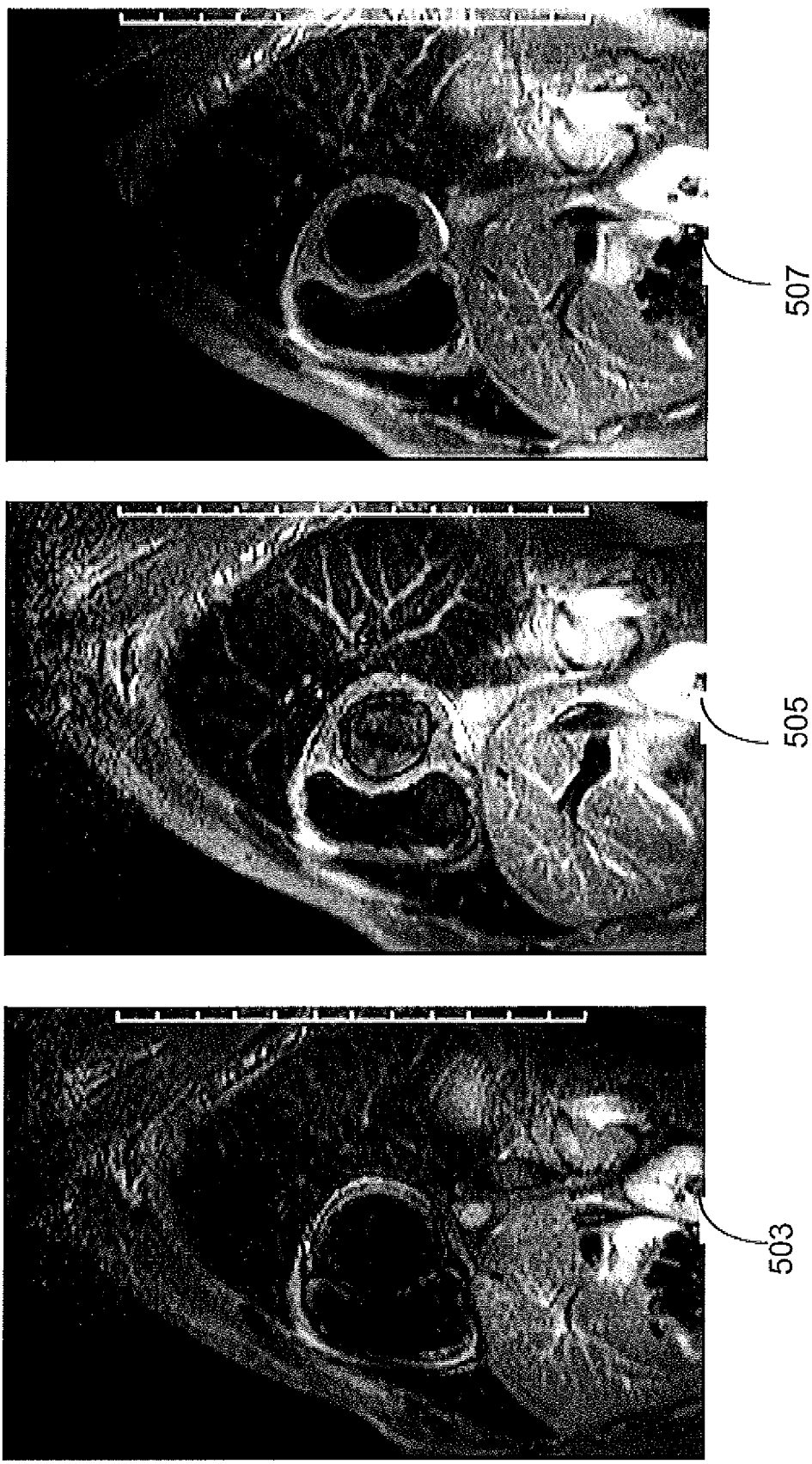
FIG. 18 shows imaging results obtained with and without the use of the system, according to invention principles.

FIG. 18 shows imaging results obtained with and without the use of the system according to invention principles. Image 503 is acquired with a known STIR sequence (that uses a slice-selective STIR pulse) performed when the heart rate is high (RR is relatively short). Image 505 depicts left and right ventricular walls that are substantially improved and is acquired using a non-selective STIR pulse according to invention principles, however, the blood in the cavity is not sufficiently nulled. Image 507 is acquired using automated parameter setting according to invention principles and indicates that the blood is properly nulled (dark) and the image is acquired during mid to end of the diastolic phase.

The use of a non-selective inversion pulse has significant benefits in image quality as the spatial match of a preparation pulse with the imaging slice is crucial with the selective inversion. The non-selective inversion removes this requirement but makes the calculation of the correct timing of the dark blood preparation more difficult. The timing calculation responds to this in the context of dark-blood prepared STIR imaging of the heart, for example. The system calculation adaptively responds to the parameters and enables an automated or semi-automated MR device setup accommodating aspects which are usually beyond the capabilities of an operator to calculate accurately, especially when the STIR with non-selective preparation is used, for example. The timing calculation uses inputs indicating desired contrast type and heart rate and selective or non-selective inversion indication to determine a timing output and automatically configure an MR imaging system for image acquisition and optimize scan duration within a heart beat to minimize motion related image quality issues.

Figure 30:
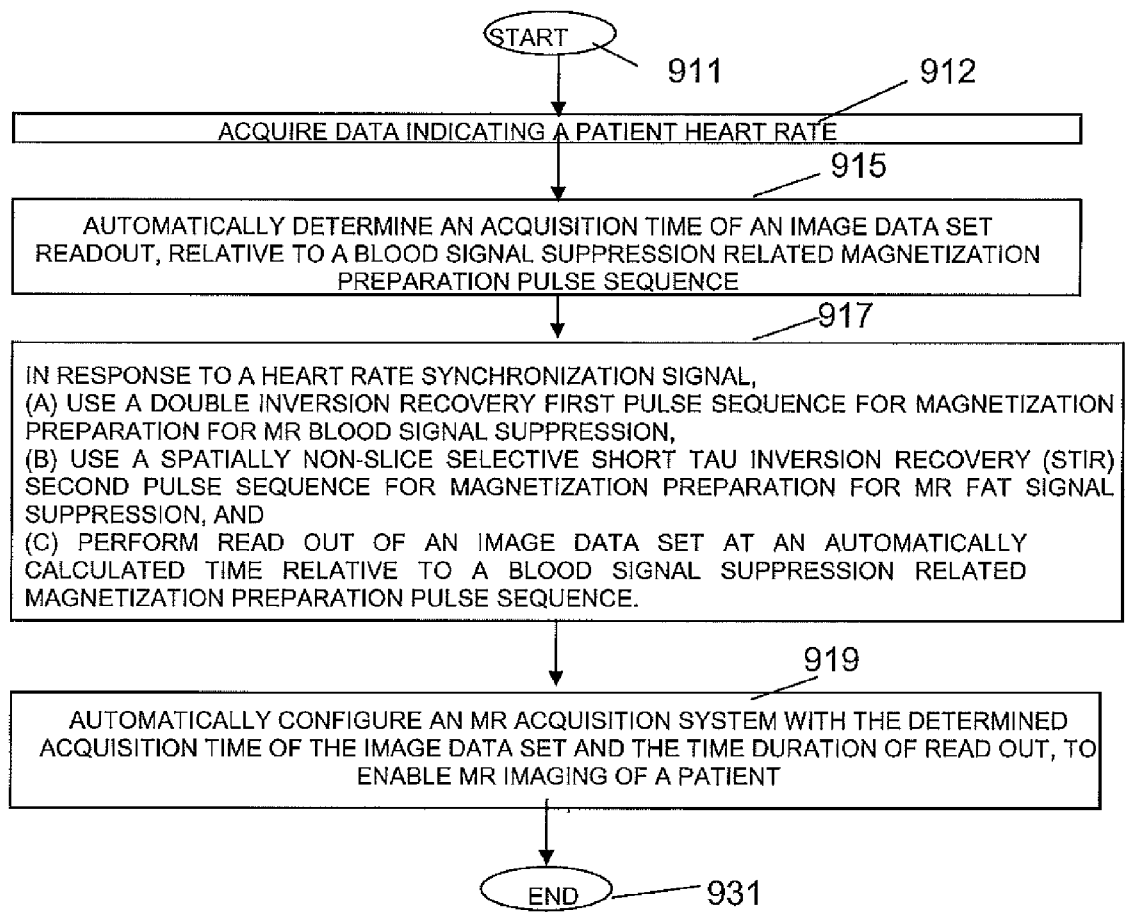
FIG. 30 shows a flowchart of a process performed by a system for automatically determining pulse sequence timing parameters for MR imaging with blood related signal suppression, according to invention principles.

FIG. 30 shows a flowchart of a process performed by system 10 (FIG. 3) for automatically determining pulse sequence timing parameters for MR imaging with blood related signal suppression. In step 912 following the start at step 911, an acquisition processor in computer 20 acquires data indicating a patient heart rate from at least one of, (a) user data entry and (b) automatically from a heart rate monitoring device. In step 915 a pulse timing processor in computer 20 of system 10 automatically determines an acquisition time of an image data set readout, relative to a blood signal suppression related magnetization preparation pulse sequence (in one embodiment comprising a non-selective inversion recovery (IR) and a slice selective IR pulse), by calculating the acquisition time in response to inputs. The inputs include, the acquired patient heart rate, data indicating a type of contrast imaging pulse sequence employed, data indicating whether an anatomical signal suppression related magnetization preparation pulse sequence (e.g., a short tau inversion recovery (STIR) fat suppression pulse sequence) used has a slice selective, or non-slice selective, data acquisition readout, data indicating whether the image acquisition is slice selective or non-slice selective and data indicating whether a blood signal suppression related magnetization preparation pulse sequence is a short tau inversion recovery (STIR) pulse sequence or a non-STIR compatible sequence. Also in one embodiment, at least one of, (a) a Turbo-Spin Echo (TSE) read out with slice-selective refocusing is used and (b) a Turbo-Spin Echo (TSE) read out with non-selective refocusing is used.

The data indicating type of contrast imaging pulse sequence indicates at least one of, (a) a longitudinal relaxation time $T_1$ associated contrast, (b) a transverse relaxation time $T_2$ associated contrast and (c) a short tau inversion recovery (STIR) contrast. The data indicating whether an anatomical signal suppression related magnetization preparation pulse sequence used has a slice selective, or non-slice selective, data acquisition readout, indicates the magnetization preparation pulse sequence is for at least one of (a) MR blood signal suppression, (b) MR fat signal suppression and (c) MR tissue signal suppression.

The pulse timing processor adaptively selects and determines a timing calculation expression from a plurality of predetermined expressions for calculating the acquisition time in response to the inputs. Thereby, the pulse timing processor automatically adaptively determines an acquisition time and duration of an image data set readout in response to a patient heart cycle indicative electrophysiological signal and in response to the inputs and input data indicating whether a selective refocusing read out or a non-selective re-focusing read out, is used. Further, the blood signal suppression related magnetization preparation pulse sequence occurs in a first heart beat cycle and the pulse timing processor automatically adaptively determines the acquisition time in response to a determination read out is to occur in the first heart beat cycle or a subsequent second heart beat cycle or a subsequent third heart beat cycle.

In step 917 in one embodiment, system 10 performs fat and blood related MR imaging signal suppression by, in response to a heart rate synchronization signal, using a double inversion recovery first pulse sequence for magnetization preparation for MR blood signal suppression. System 10 uses a spatially non-slice selective short tau inversion recovery (STIR) second pulse sequence for magnetization preparation for MR fat signal suppression, and performs read out of an image data set at an automatically calculated time relative to a blood signal suppression related magnetization preparation pulse sequence. In step 919, an output processor in computer 20 automatically configures the MR acquisition system with the determined acquisition time of the image data set and the time duration of read out, to enable MR imaging of a patient. The process of FIG. 30 terminates at step 931.

A processor as used herein is a device for executing machine-readable instructions stored on a computer readable medium, for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example, and is conditioned using executable instructions to perform special purpose functions not performed by a general purpose computer. A processor may be coupled (electrically and/or as comprising executable components) with any other processor enabling interaction and/or communication there-between. A user interface processor or generator is a known element comprising electronic circuitry or software or a combination of both for generating display images or portions thereof. A user interface comprises one or more display images enabling user interaction with a processor or other device.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A graphical user interface (GUI), as used herein, comprises one or more display images, generated by a display processor and enabling user interaction with a processor or other device and associated data acquisition and processing functions.

The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity.

The system and processes of FIGS. 3 and 6-30 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. A Magnetic Resonance Imaging (MRI) system employs dark-blood (DB) and dark-blood inversion recovery pulse sequences and automatically calculates optimal protocol parameters including timing parameters, temporal resolution, dark blood thickness, and trigger pulse parameters for the pulse sequences as a function of patient heart rate simplifying operation of the pulse sequences by an MRI scanner operator and improving image quality for different heart rates. Further, the processes and applications may, in alternative embodiments, be located on one or more (e.g., distributed) processing devices on a network linking the units of FIG. 3. Any of the functions and steps provided in FIGS. 3 and 6-30 may be implemented in hardware, software or a combination of both.

What is claimed is:

1. A system for automatically determining pulse sequence timing parameters for MR imaging with an electro cardiogram (ECG) gated dark-blood turbo-spin echo (TSE) pulse sequence, comprising:
   an acquisition processor configured to continuously detect an R-wave of an ECG signal of a patient and provide a patient heart rate;
   a memory configured to store a first set of predetermined parameters; and
   a pulse timing processor configured to use the first set of predetermined parameters in the memory and calculate a second set of parameters to determine the pulse sequence timing parameters of said ECG-gated dark blood TSE pulse sequence as a function of:
      (a) the provided patient heart rate;
      (b) a type of image contrast employed; and
      (c) a type of data acquisition readout.

2. A system according to claim 1, wherein
said pulse timing processor automatically determines the pulse sequence timing parameters from trigger pulse, temporal resolution and turbo-factor, dark-blood thickness, beginning of dark-blood preparation relative to the heart's R-wave, beginning of the acquisition time interval relative to the heart's R-wave, an algorithm to place the acquisition time interval when cardiac motion is minimal, and simultaneously minimizing the blood signal to produce dark-blood motion-minimized turbo-spin echo images.

3. A system according to claim 1, wherein
said pulse timing processor automatically determines the pulse sequence timing parameters by calculating said acquisition time interval and time of initiation of a blood signal suppression related magnetization preparation pulse sequence in response to inputs.

4. A system according to claim 1, wherein
said pulse timing processor determines the pulse sequence timing parameters substantially between an image data set readout and said blood signal suppression related magnetization preparation pulse sequence comprising both a non-selective inversion recovery (IR) and a slice selective IR pulse.

5. A system according to claim 1, wherein
said pulse timing processor determines the pulse sequence timing parameters in response to said type of contrast imaging pulse sequence and said type of contrast imaging pulse sequence enhances image luminance contrast of anatomical elements based on change in a selected one of, (a) a longitudinal relaxation time $T_1$ and (b) a transverse relaxation time $T_2$.

6. A system according to claim 1, wherein
said pulse timing processor determines the pulse sequence timing parameters in response to said data indicating whether an anatomical signal suppression related magnetization preparation pulse sequence used has a slice selective, or non-slice selective, data acquisition readout additionally indicating the magnetization preparation pulse sequence is for at least one of, (a) MR blood signal suppression, (b) MR fat signal suppression and (c) MR tissue signal suppression.

7. A system according to claim 1, wherein
said pulse timing processor determines the pulse sequence timing parameters in response to selection of said anatomical signal suppression related magnetization preparation pulse sequence as a short tau inversion recovery (STIR) fat suppression pulse sequence.

8. A system according to claim 1, wherein
said pulse timing processor automatically determines a time duration of read out of an image data set.

9. A system according to claim 8, including
an output processor for automatically configuring an MR acquisition system with the determined the pulse sequence timing parameters and a time duration of read out, to enable MR imaging of a patient.

10. A system according to claim 1, including
an output processor for automatically configuring an MR acquisition system with the determined the pulse sequence timing parameters, to enable MR imaging of a patient.

11. A system according to claim 1, wherein
said pulse timing processor automatically determines said pulse sequence timing parameters in response to input data indicating whether a selective refocusing read out or a non-selective re-focusing read out, is used.

12. A system according to claim 11, wherein
said pulse timing processor automatically determines said pulse sequence timing parameters in response to said selective refocusing read out comprising a Turbo-Spin Echo (TSE) read out with slice-selective refocusing and said non-selective re-focusing read out comprises a Turbo-Spin Echo (TSE) read out with non-selective refocusing.

13. A system according to claim 1, wherein
said pulse timing processor determines said pulse sequence timing parameters substantially between an image data set readout and said blood signal suppression related magnetization preparation pulse sequence occurring in a first heart beat cycle and
said pulse timing processor automatically determines said pulse sequence timing parameters in response to the determined acquisition time interval indicating read out is to occur in said first heart beat cycle or a subsequent second heart beat cycle succeeding said first heart beat cycle or a successive third heart beat cycle subsequent to said second heart beat cycle.

14. A system according to claim 1, wherein
said pulse timing processor calculates said pulse sequence timing parameters using a timing calculation expression and
said pulse timing processor adaptively selects said timing calculation expression from a plurality of predetermined expressions.

15. A system according to claim 1, including
an MR imaging system for acquiring said an image data set in response to the determined pulse sequence timing parameters.

16. A method for automatically determining pulse sequence timing parameters for MR imaging with an electro cardiogram (ECG) gated dark-blood turbo-spin echo (TSE) pulse sequence, comprising:
continuously detecting an R-wave of an ECG signal of a patient and provide a patient heart rate;
storing a first set of predetermined parameters; and
automatically determining the pulse sequence timing parameters of said ECG-gated dark blood TSE pulse sequence by using the first set of predetermined parameters in the memory and calculating a second set of parameters, wherein the pulse sequence timing parameters are determined as a function of:
(a) the provided patient heart rate;
(b) a type of image contrast employed; and
(c) a type of data acquisition readout.

17. A system according to claim 1, wherein
the ECG-gated dark-blood TSE pulse sequence comprises a non-slice selective inversion pulse which nulls of fat signal, and
the pulse timing processor is further configured to calculate a beginning of said non-slice selective inversion pulse relative to the beginning of an acquisition time interval to minimize the fat signal.

18. A system according to claim 1, wherein
the type of image contrast employed is at least one of a spin-lattice relaxation time T1 and a spin-spin relaxation time T2.

19. The system of claim 1 wherein the type of data acquisition readout is slice selective.

20. The system of claim 1 wherein the type of data acquisition readout is non-slice selective.

21. The system of claim 1 wherein the type of data acquisition readout is a TSE readout.

* * * * *